US006335164B1

(12) United States Patent
Kigawa et al.

(10) Patent No.: US 6,335,164 B1
(45) Date of Patent: Jan. 1, 2002

(54) METHODS FOR TARGETING, ENRICHING, DETECTING AND/OR ISOLATING TARGET NUCLEIC ACID SEQUENCE USING RECA-LIKE RECOMBINASE

(75) Inventors: Koji Kigawa; Mikayo Yamanaka; Kayo Kusumi; Eli Mukai; Kazuaki Obata, all of Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/147,751

(22) PCT Filed: Aug. 29, 1997

(86) PCT No.: PCT/JP97/03019

§ 371 Date: May 18, 1999

§ 102(e) Date: May 18, 1999

(87) PCT Pub. No.: WO98/08975

PCT Pub. Date: Mar. 5, 1998

(30) Foreign Application Priority Data

Aug. 29, 1996 (JP) .............................................. 8-229061
Dec. 26, 1996 (JP) .............................................. 8-347090

(51) Int. Cl.$^7$ ................................................ C12Q 1/68
(52) U.S. Cl. ........................... 435/6; 435/6; 435/320.1; 435/172.3; 435/4; 435/240.2; 435/69.1; 435/172.1; 530/350; 514/44
(58) Field of Search ...................... 435/6, 172.3, 240.2, 435/4, 172.1, 320.1, 69.1; 530/350; 514/44

(56) References Cited

U.S. PATENT DOCUMENTS

| 4,888,274 A | 12/1989 | Radding et al. ................ 435/6 |
| 5,223,414 A | 6/1993 | Zarling et al. ................ 435/91 |
| 5,468,629 A | 11/1995 | Calhoun .................. 435/172.3 |

FOREIGN PATENT DOCUMENTS

| EP | 0 687 738 A1 | 12/1994 |
| EP | 0 687 738 | 7/1995 |
| WO | 91/17267 | 11/1991 |
| WO | 93/02244 | 2/1993 |
| WO | WO 93/05177 | 3/1993 |
| WO | WO 93/05178 | 3/1993 |
| WO | 93/22443 | 11/1993 |

OTHER PUBLICATIONS

T. Shibata et al. Cell Technology, vol. 9, No. 4, "Mechanism in in vitro Genetic Recombination Reactions by recA Protein," pp. 281–292 (1990).
C. S. Kowalczykowski Annu. rev. Biophys. Chem., vol. 20, "Biochemistry of Genetic Recombination: Energetics and Mechanism of DNA Strand Exchange," pp. 539–575 (1991).
T. Yonesaki et al. Eur. J. Biochem., vol. 148, "Purification and some of the functions of the products of bacteriophage T4 recombination genes, uvsX and uvsY," pp. 127–134 (1985).

E. Kmiec et al. Cell, vol. 29, "Homologous Pairing of DNA Molecules Promoted by a Protein from Ustilago," pp. 367–374 (1982).
C. M. Lovett, Jr. J. Biol. Chem., vol. 260, No. 6, "Purification of a RecA Protein Analogue from *Bacillus subtilis*," pp. 3305–3313 (1985).
Charles M. Radding, Helical RecA Nucleoprotein Filaments Mediate Homologous Pairing and Strand Exchange, Biochimicaet Biophysica Acta, 1008 (1989), pp. 131–145.
Charles Meyer Radding, Helical Interactions in Homologous Pairing and Strand Exchange Driven by RecA Protein, The Journal of Biological Chemistry, vol. 266, No. 9, pp. 5355–5358, Mar. 1991.
EFIM I. Golub, et al., Joints Formed by RecA Protein From Oligonucleotides and Duplex DNA Block Initiation and Elongation of Transcription, Nucleic Acids Research, vol. 20, No. 12, pp. 3121–3125, 1992.
Takehiko Shibata, et al., Purification of RecA Protein From *Escherichia coli*, Method in Enzymology, vol. 100, pp. 197–209.
Murty v.v.S. Madiraju, et al., Properties of a Mutant RecA–encoded Protein Reveal a Possible Role for *Escherichia coli* RecF–encoded Protein in Genetic Recombination, PNAC, vol. 85, pp. 6592–6596, Sep. 1988.
Hitoshi Kawashima, et al., Functional Domains of *Escherichia coli* RecA Protein Deduced From the Mutational Sites in the Gene, Mol Gen Gennet, vol. 193, pp. 288–292, 1984.
Eric B. Kmiec, et al., Synapsis Promoted by Ustilago Rec1 Protein, Cell, vol. 36, pp. 593–598, Mar. 1984, pp. 593–598.
Evelina Angov, et al., The RecA Gene From the Thermophile Thermus Aquaticus YT–1: Cloning, Expression and Characterization Journal of Bacteriology, pp. 1405–1412, Mar. 1994.
Ryuichi Kato, et al., RecA Protein From an Extremely Thermophilic Bacterium, Thermus Thermophilus HB8, J. Biochem, vol. 114, pp. 926–929, 1993.
Akira Shinohara, et al., Cloning of Human, Mouse and Fission Yeast Recombination Genes Homologous to RAD51 and RecA, Nature Genetics, vol. 4, pp. 239–243, Jul. 1993.
Seiki Kuramitsu, et al., A Large–Scale Preparation and Some Physicochemical Properties of RecA Protein, J. Biochem, vol. 90, pp. 1033–1045, 1981.

(List continued on next page.)

*Primary Examiner*—Karen Cochrane Carlson
*Assistant Examiner*—Hope A. Robinson
(74) *Attorney, Agent, or Firm*—Foley & Lardner

(57) ABSTRACT

A method for targeting, enriching, detecting and isolating a double-stranded nucleic acid target sequence by adding heterologous probes to the reaction system along with the reduced amount of homologous probes in the process of homologous pairing and/or strand exchange between the homologous probe and the target sequence in the presence of a RecA-like recombinase.

58 Claims, No Drawings

OTHER PUBLICATIONS

Stephen C. Kowalczykowski, et al., DNA–strand exchange promoted by RecA protein in the absence of ATP: Impliations for the mechanism of energy transduction in protein–promoted nucleic acid transactions, Proc. Natl. Acad. Sci. USA, vol. 92, pp 3478–3482, Apr. 1995.

Patrice L. Moreau, et al., RecA Protein–promoted Cleavage of LexA Repressor in the Presence of ADP and Structural Analogues of Inorganic Phosphate, the Fluoride Complexes of Aluminum and Beryllium, The Journal of Biological Chemistry, vol. 264, No. 4, pp. 2302–2306, Feb. 1989.

Lance J. Ferrin, et al., Long–range mapping of gaps and telomeres with RecA–assisted restriction endonuclease (RARE) cleavage, Nature Genetics, vol. 6, pp. 379–383, Apr. 1994.

Bernard M.J. Revet, et al., Homologous DNA Targeting withRecA Protein–coated Short DNA Probes and Electron Microscope Mapping on Linear Duplex Molecules, J. Mol. Biol., vol. 232, pp. 779–791, 1993.

Michael Koob, et al., RecA–AC: single–site cleavage of plasmids and chromosomes at any predetermined restriction site, Nucleic Acids Research, vol. 20, No. 21, pp. 5831–5836, 1992.

Mikhail A. Podyminogin, et al., Sequence–Specific Covalent Modification of DNA by Cross–Linking Oligonucleotides. Catalysis by RecA and Implication for the Mechanism of Synaptic Joint Formation, Biochemistry, vol. 34, pp. 13098–13108, 1995.

EFIM I. Golub, et al., Inhibition of RNA polymerase II transcription by oligonucleotide–RecA protein filaments targeted to promoter sequences, Proc. Natl. Acad. Sci., USA, vol. 90, pp. 7186–7190, Aug. 1993.

Rina Zakut–Houri, et al., Human p53 cellular tumor antigen: cDNA sequence and expression in COS cells, The EMBO Journal, vol. 4, No. 5, pp. 1251–1251, 1985.

Hiroaki Inoue, et al., Gene, High efficiency transformation of *Escherichia coli* with plasmids, vol. 96, pp. 23–28, 1990.

Basil Rigas, et al., Rapid Plasmid Library Screening Using RecA–Coated Biotinylated Probes, PNAC, vol. 83, pp. 9591–9595, Dec. 1986.

Peggy Hsieh, et al., The Synapsis Event in the Homologous Pairing of DNAs: RecA Recognizes and Pairs Less Then One Helical Repeat of DNA, PNAC, vol. 89, pp. 6492–6496, Jul. 1992.

Lance J. Ferrin, et al., Selective Cleavage of Human DNA: RecA–Assisted Restriction Endonuclease (RARE) Cleavage Science, vol. 254, pp. 1494–1497, Dec. 1991.

Elissa P. Sena, et al., Targeting in Linear DNA Duplexes With Two Complementary Probe Strands for Hybrid Stability, Nature Genetics, vol. 3, pp. 365–372.

Veneetha . Jayasena, et al., Complement–stabilized D–loop RecA–catalyzed Stable Pairing of Linear DNA Molecules at Internal Sites, pp. 1015–1024.

Dwight P. Kirkpatrick, et al., RecA Protein Promotes Rapid RNA–DNA Hybridization in Heterogeneous RNA Mixtures, pp. 4347–4353.

Dwight P. Kirkpatrick, et al., RNA–DNA Hybridization Promoted by *E.coli* RecA Protein, Nucleic Acid Research, vol. 20, No. 16, pp. 4339–4346, 1992.

Martin Teintze, et al., RecA–Assisted Rapid Enrichment of Specific Clones From Model DNA Libraries, Biochemical and Biophysical Research Communications, vol. 211, No. 3, pp. 804–811, Jun. 26, 1995.

Siu Sing Tsang, et al., Networks of DNA and RecA Protein Are Intermediates in Homologous Pairing, Bichemistry, vol. 24, pp. 3226–3232, 1985.

David K. Gonda, et al., The Mechanism of the Search for Homology Promoted by RecA Protein, The Journal of Biological Chemistry, vol. 261, No. 28, pp. 13087–13096, Oct. 1986.

Samson A. Chow, et al., Ionic Inhibition of Formation of RecA Nucleoprotein Networks Blocks Homologous Pairing, PNAC, vol. 82, pp. 5646–5650, Sep. 1985.

Saul M. Honigberg, et al., Ability of RecA Protein to Promote a Search for Rare Sequences in Duplex DNA, PNAC, vol. 83, pp. 9586–9590, Dec. 1986.

```
                              SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
         (A) LENGTH: 275 base pairs
         (B) TYPE: nucleic acid
         (C) STRANDEDNESS: double
         (D) TOPOLOGY: linear (ii) MOLECULE TYPE: cDNA to mRNA (xi) SEQUENCE DESCRIPTION: SEQ ID NO:1:

CCTTGCCGTC CCAAGCAATG GATGATTTGA TGCTGTCCCC GGACGATATT GAACAATGGT      60

TCACTGAAGA CCCAGGTCCA GATGAAGCTC CCAGAATGCC AGAGGCTGCT CCCCGCGTGG     120

CCCCTGCACC AGCAGCTCCT ACACCGGCGG CCCCTGCACC AGCCCCCTCC TGGCCCCTGT     180

CATCTTCTGT CCCTTCCCAG AAAACCTACC AGGGCAGCTA CGGTTTCCGT CTGGGCTTCT     240

TGCATTCTGG GACAGCCAAG TCTGTGACTT GCACG                               275

(2) INFORMATION FOR SEQ ID NO:2:

(i) SEQUENCE CHARACTERISTICS:
         (A) LENGTH: 60 base pairs
         (B) TYPE: nucleic acid
         (C) STRANDEDNESS: double
         (D) TOPOLOGY: linear (ii) MOLECULE TYPE: cDNA to mRNA (xi) SEQUENCE DESCRIPTION: SEQ ID NO:2:

AGCTACGGTT TCCGTCTGGG CTTCTTGCAT TCTGGGACAG CCAAGTCTGT GACTTGCACG      60
```

(2) INFORMATION FOR SEQ ID NO:3:

(i) SEQUENCE CHARACTERISTICS:
        (A) LENGTH: 500 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
GATGAGTTCG TGTCCGTACA ACTGGCGTAA TCATGGCCCT TCGGGGCCAT TGTTTCTCTG      60

TGGAGGAGTC CATGACGAAA GATGAACTGA TTGCCCGTCT CCGCTCGCTG GGTGAACAAC     120

TGAACCGTGA TGTCAGCCTG ACGGGACGA AAGAAGAACT GGCGCTCCGT GTGGCAGAGC      180

TGAAAGAGGA GCTTGATGAC ACGGATGAAA CTGCCGGTCA GGACACCCCT CTCAGCCGGG     240

AAAATGTGCT GACCGGACAT GAAAATGAGG TGGGATCAGC GCAGCCGGAT ACCGTGATTC     300

TGGATACGTC TGAACTGGTC ACGGTCGTGG CACTGGTGAA GCTGCATACT GATGCACTTC     360

ACGCCACGCG GGATGAACCT GTGGCATTTG TGCTGCCGGG AACGGCGTTT CGTGTCTCTG     420

CCGGTGTGGC AGCCGAAATG ACAGAGCGCG GCCTGGCCAG AATGCAATAA CGGGAGGCGC     480

TGTGGCTGAT TTCGATAACC                                                 500
```

(2) INFORMATION FOR SEQ ID NO:4:

(i) SEQUENCE CHARACTERISTICS:
        (A) LENGTH: 1393 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
GCGGCACGGA GTGGAGCAAG CGTGACAAGT CCACGTATGA CCCGACCGAC GATATCGAAG      60

CCTACGCGCT GAACGCCAGC GGTGTGGTGA ATATCATCGT GTTCGATCCG AAAGGCTGGG     120

CGCTGTTCCG TTCCTTCAAA GCCGTCAAGG AGAAGCTGGA TACCCGTCGT GGCTCTAATT     180

CCGAGCTGGA GACAGCGGTG AAAGACCTGG GCAAAGCGGT GTCCTATAAG GGGATGTATG     240

GCGATGTGGC CATCGTCGTG TATTCCGGAC AGTACGTGGA AAACGGCGTC AAAAAGAACT     300

TCCTGCCGGA CAACACGATG GTGCTGGGGA ACACTCAGGC ACGCGGTCTG CGCACCTATG     360

GCTGCATTCA GGATGCGGAC GCACAGCGCG AAGGCATTAA CGCCTCTGCC CGTTACCCGA     420

AAAACTGGGT GACCACCGGC GATCCGGCGC GTGAGTTCAC CATGATTCAG TCAGCACCGC     480

TGATGCTGCT GGCTGACCCT GATGAGTTCG TGTCCGTACA ACTGGCGTAA TCATGGCCCT     540

TCGGGGCCAT TGTTTCTCTG TGGAGGAGTC CATGACGAAA GATGAACTGA TTGCCCGTCT     600

CCGCTCGCTG GGTGAACAAC TGAACCGTGA TGTCAGCCTG ACGGGACGA AAGAAGAACT      660

GGCGCTCCGT GTGGCAGAGC TGAAAGAGGA GCTTGATGAC ACGGATGAAA CTGCCGGTCA     720

GGACACCCCT CTCAGCCGGG AAAATGTGCT GACCGGACAT GAAAATGAGG TGGGATCAGC     780

GCAGCCGGAT ACCGTGATTC TGGATACGTC TGAACTGGTC ACGGTCGTGG CACTGGTGAA     840

GCTGCATACT GATGCACTTC ACGCCACGCG GGATGAACCT GTGGCATTTG TGCTGCCGGG     900

AACGGCGTTT CGTGTCTCTG CCGGTGTGGC AGCCGAAATG ACAGAGCGCG GCCTGGCCAG     960

AATGCAATAA CGGGAGGCGC TGTGGCTGAT TTCGATAACC TGTTCGATGC TGCCATTGCC    1020
```

```
CGCGCCGATG AAACGATACG CGGGTACATG GAACGTCAG CCACCATTAC ATCCGGTGAG    1080

CAGTCAGGTG CGGTGATACG TGGTGTTTTT GATGACCCTG AAAATATCAG CTATGCCGGA    1140

CAGGGCGTGC GCGTTGAAGG CTCCAGCCCG TCCCTGTTTG TCCGGACTGA TGAGGTGCGG    1200

CAGCTGCGGC GTGGAGACAC GCTGACCATC GGTGAGGAAA ATTTCTGGGT AGATCGGGTT    1260

TCGCCGGATG ATGGCGGAAG TTGTCATCTC TGGCTTGGAC GGGGCGTACC GCCTGCCGTT    1320

AACCGTCGCC GCTGAAAGGG GGATGTATGG CCATAAAAGG TCTTGAGCAG GCCGTTGAAA    1380

ACCTCAGCCG TAT                                                       1393
```

(2) INFORMATION FOR SEQ ID NO:5:

(i) SEQUENCE CHARACTERISTICS:
        (A) LENGTH: 308 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
AGGTGCGGTG ATACGTGGTG TTTTTGATGA CCCTGAAAAT ATCAGCTATG CCGGACAGGG      60

CGTGCGCGTT GAAGGCTCCA GCCCGTCCCT GTTTGTCCGG ACTGATGAGG TGCGGCAGCT     120

GCGGCGTGGA GACACGCTGA CCATCGGTGA GGAAAATTTC TGGGTAGATC GGGTTTCGCC     180

GGATGATGGC GGAAGTTGTC ATCTCTGGCT TGGACGGGGC GTACCGCCTG CCGTTAACCG     240

TCGCCGCTGA AGGGGGATG TATGGCCATA AAAGGTCTTG AGCAGGCCGT TGAAAACCTC      300

AGCCGTAT                                                              308
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:6:

```
CCTTGCCGTC CAAGCAATG GATGATTTGA                                        30
```

(2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AACGGCGTTT CGTGTCTCTG CCGGTGTGGC AGCCGAAATG ACAGAGCGCG GCCTGGCCAG      60
```

(2) INFORMATION FOR SEQ ID NO:8:

(i) SEQUENCE CHARACTERISTICS:
        (A) LENGTH: 1317 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:8:

| | | | | | |
|---|---|---|---|---|---|
| GTCTAGAGCC | ACCGTCCAGG | GAGCAGGTAG | CTGCTGGGCT | CCGGGGACAC | TTTGCGTTCG | 60
| GGCTGGGAGC | GTGCTTTCCA | CGACGGTGAC | ACGCTTCCCT | GGATTGGCAG | CCAGACTGCC | 120
| TTCCGGGTCA | CTGCCATGGA | GGAGCCGCAG | TCAGATCCTA | GCGTCGAGCC | CCCTCTGAGT | 180
| CAGGAAACAT | TTTCAGACCT | ATGGAAACTA | CTTCCTGAAA | CAACGTTCT | GTCCCCCTTG | 240
| CCGTCCCAAG | CAATGGATGA | TTTGATGCTG | TCCCCGACG | ATATTGAACA | ATGGTTCACT | 300
| GAAGACCCAG | GTCCAGATGA | AGCTCCCAGA | ATGCCAGAGG | CTGCTCCCCG | CGTGGCCCCT | 360
| GCACCAGCAG | CTCCTACACC | GGCGGCCCCT | GCACCAGCCC | CCTCCTGGCC | CCTGTCATCT | 420
| TCTGTCCCTT | CCCAGAAAAC | CTACCAGGGC | AGCTACGGTT | CCGTCTGGG | CTTCTTGCAT | 480
| TCTGGGACAG | CCAAGTCTGT | GACTTGCACG | TACTCCCCTG | CCCTCAACAA | GATGTTTTGC | 540
| CAACTGGCCA | AGACCTGCCC | TGTGCAGCTG | TGGGTTGATT | CCACACCCCC | GCCCGGCACC | 600
| CGCGTCCGCG | CCATGGCCAT | CTACAAGCAG | TCACAGCACA | TGACGGAGGT | TGTGAGGCGC | 660
| TGCCCCCACC | ATGAGCGCTG | CTCAGATAGC | GATGGTCTGG | CCCCTCCTCA | GCATCTTATC | 720
| CGAGTGGAAG | GAAATTTGCG | TGTGGAGTAT | TTGGATGACA | GAAACACTTT | TCGACATAGT | 780
| GTGGTGGTGC | CCTATGAGCC | GCCTGAGGTT | GGCTCTGACT | GTACCACCAT | CCACTACAAC | 840
| TACATGTGTA | ACAGTTCCTG | CATGGGCGGC | ATGAACCAGA | GGCCCATCCT | CACCATCATC | 900
| ACACTGGAAG | ACTCCAGTGG | TAATCTACTG | GGACGGAACA | GCTTTGAGGT | GCGTGTTTGT | 960
| GCCTGTCCTG | GGAGAGACCG | GCGCACAGAG | GAAGAGAATC | TCCGCAAGAA | AGGGGAGCCT | 1020
| CACCACGAGC | TGCCCCCAGG | GAGCACTAAG | CGAGCACTGC | CAACAACAC | CAGCTCCTCT | 1080
| CCCCAGCCAA | GAAGAAACC | ACTGGATGGA | GAATATTTCA | CCCTTCAGAT | CCGTGGGCGT | 1140
| GAGCGCTTCG | AGATGTTCCG | AGAGCTGAAT | GAGGCCTTGG | AACTCAAGGA | TGCCCAGGCT | 1200
| GGGAAGGAGC | CAGGGGGGAG | CAGGGCTCAC | TCCAGCCACC | TGAAGTCCAA | AAAGGGTCAG | 1260
| TCTACCTCCC | GCCATAAAAA | ACTCATGTTC | AAGACAGAAG | GGCCTGACTC | AGACTGA | 1317

(2) INFORMATION FOR SEQ ID NO:9:

(i) SEQUENCE CHARACTERISTICS:
        (A) LENGTH: 410 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:9:

| | | | | | |
|---|---|---|---|---|---|
| CCTTGCCGTC | CCAAGCAATG | GATGATTTGA | TGCTGTCCCC | GGACGATATT | GAACAATGGT | 60
| TCACTGAAGA | CCCAGGTCCA | GATGAAGCTC | CCAGAATGCC | AGAGGCTGCT | CCCCGCGTGG | 120
| CCCCTGCACC | AGCAGCTCCT | ACACCGGCGG | CCCCTGCACC | AGCCCCCTCC | TGGCCCCTGT | 180
| CATCTTCTGT | CCCTTCCCAG | AAAACCTACC | AGGGCAGCTA | CGGTTTCCGT | CTGGGCTTCT | 240
| TGCATTCTGG | GACAGCCAAG | TCTGTGACTT | GCACGTACTC | CCCTGCCCTC | AACAAGATGT | 300
| TTTGCCAACT | GGCCAAGACC | TGCCCTGTGC | AGCTGTGGGT | TGATTCCACA | CCCCGCCCG | 360
| GCACCCGCGT | CCGCGCCATG | GCCATCTACA | AGCAGTCACA | GCACATGACG | | 410

(2) INFORMATION FOR SEQ ID NO:10:

(i) SEQUENCE CHARACTERISTICS:
        (A) LENGTH: 779 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:10:

```
CCTTGCCGTC CCAAGCAATG GATGATTTGA TGCTGTCCCC GGACGATATT GAACAATGGT      60
TCACTGAAGA CCCAGGTCCA GATGAAGCTC CAGAATGCC AGAGGCTGCT CCCCGCGTGG      120
CCCCTGCACC AGCAGCTCCT ACACCGGCGG CCCCTGCACC AGCCCCCTCC TGGCCCCTGT      180
CATCTTCTGT CCCCTTCCCAG AAAACCTACC AGGGCAGCTA CGGTTTCCGT CTGGGCTTCT      240
TGCATTCTGG GACAGCCAAG TCTGTGACTT GCACGTACTC CCCTGCCCTC AACAAGATGT      300
TTTGCCAACT GGCCAAGACC TGCCCTGTGC AGCTGTGGGT TGATTCCACA CCCCCGCCCG      360
GCACCCGCGT CCGCGCCATG GCCATCTACA AGCAGTCACA GCACATGACG GAGGTTGTGA      420
GGCGCTGCCC CCACCATGAG CGCTGCTCAG ATAGCGATGG TCTGGCCCCT CCTCAGCATC      480
TTATCCGAGT GGAAGGAAAT TTGCGTGTGG AGTATTTGGA TGACAGAAAC ACTTTTCGAC      540
ATAGTGTGGT GGTGCCCTAT GAGCCGCCTG AGGTTGGCTC TGACTGTACC ACCATCCACT      600
ACAACTACAT GTGTAACAGT TCCTGCATGG GCGGCATGAA CCAGAGGCCC ATCCTCACCA      660
TCATCACACT GGAAGACTCC AGTGGTAATC TACTGGGACG GAACAGCTTT GAGGTGCGTG      720
TTTGTGCCTG TCCTGGGAGA GACCGGCGCA CAGAGGAAGA GAATCTCCGC AAGAAAGGG      779
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:11:

```
CCTTGCCGTC CCAAGCAATG GATGA                                            25
```

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:12:

```
CGTGCAAGTC ACAGACTTGG CTGTC                                            25
```

(2) INFORMATION FOR SEQ ID NO:13:

(i) SEQUENCE CHARACTERISTICS:
        (A) LENGTH: 25 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:13:

AGCTACGGTT TCCGTCTGGG CTTCT                                              25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:14:

CGTCATGTGC TGTGACTGCT TGTAG                                              25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:15:

CCCTTTCTTG CGGAGATTCT CTTCC                                              25

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:16:

GTCTAGAGCC ACCGTCCAGG GAGCA                                              25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:17:

TCAGTCTGAG TCAGGCCCTT CTGTC                                              25
```

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:18:

GATGAGTTCG TGTCCGTACA ACTGG                                      25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:19:

GGTTATCGAA ATCAGCCACA GCGCC                                      25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:20:

GCGGCACGGA GTGGAGCAAG CGTGA                                      25

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide primer"

(xi) SEQUENCE DESCRIPTION: SEQ ID NO:21:

ATACGGCTGA GGTTTTCAAC GGCCT                                      25

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION: /desc = "Oligonucleotide primer"

(xi) SEQUENCE DESCRIPTION: SEQ ID NO:22:

AGGTGCGGTG ATACGTGGTG TTTTT                                            25
```

METHODS FOR TARGETING, ENRICHING, DETECTING AND/OR ISOLATING TARGET NUCLEIC ACID SEQUENCE USING RECA-LIKE RECOMBINASE

BACKGROUND OF THE INVENTION

1. Area of the Art

The invention relates generally to methods for targeting, enriching, detecting and/or isolating target nucleic acid sequence using RecA-like recombinase, and specifically to methods for targeting, enriching, detecting and/or isolating double-stranded nucleic acid target sequence using RecA-like recombinase in the presence of both a homologous probe and a heterologous probe.

2. Description of the Prior Art

A variety of recombinases, which catalyze in vitro homologous pairing and/or exchange of DNA strands, have been isolated from various prokaryotes and eukaryotes. Among these recombinases, RecA protein, a recombinase derived from *Escherichia coli*, has been extensively investigated. (Shibata T., Cell Technology, 9, No. 4, 281–291 (1990)). RecA protein is known to catalyze in vitro homologous pairing of single-stranded DNA with double-stranded DNA and thus to generate homologously paired triple-stranded DNA or other triple-stranded joint DNA molecules. (Rigas B., et al., Proc. Natl. Acad. Sci. USA, 83: 9591–9595 (1986); Hsieh P. et al., Proc. Natl. Acad. Sci. USA, 89: 6492–6496 (1992); Ferrin L. J. et al., Science, 254: 1494–1497 (1991), etc. ). RecA protein is also reported to catalyze the formation of a four-stranded DNA structure known as a double D-loop. In this reaction, two types of complimentary single-stranded DNA are used as homologous probes to target double-stranded DNA, which has a homologous site for the single-stranded DNA probe. (Sena E. P., Nature Genetics, 3: 365–372 (1993); Jayasena V. K. et al., J. Mol. Biol., 230:1015 (1993)). In addition to DNA-DNA hybridization, RecA protein can also promote RNA-DNA hybridization. For example, single-stranded DNA coated with RecA protein can recognize complimentarily with naked RNA (Kirkpatrick and Radding, 1992; Kirkpatrick et al., 1992).

By utilizing the property of RecA protein, methods have been developed for isolating specific double-stranded target DNA existing in a solution at a very low level (at a molar ratio of 1:50 molecules to 1: several hundred molecules) (Rigas B. et al., Proc. Natl. Acad. Sci. USA, 83: 9591–9595 (1986); Teintze M. et al., Biochem. Biophys. Res. Commun., 211: 804–811 (1995); U.S. Pat. No. 4,888,274). In situ hybridization methods have also been developed for detecting double-stranded target DNA in a fixed cell (WO 93/05177). These methods use RecA to mediate homologous paring between the target DNA and a homologous probe containing a sequence sufficiently complementary to the target DNA to form a homologous probe/target DNA complex.

Homologous pairing that is catalyzed by a recombinase, such as RecA protein, leads to the formation of networks (coaggregates) comprising RecA proteins, total DNA (target DNA+heterologous DNA) and homologous probes in the system (Tsang S. S. et al., Biochemistry, 24: 3226–3232 (1985); Gonda D. K. et al., J. Biol. Chem., 261: 13087–13096; Chow S. A. et al., Proc Natl. Acad. Sci. USA, 82: 5646–5650 (1985)). The efficiency of the homologous pairing occurring between double-stranded target DNA and single-stranded nucleic acid (homologous probe), which is complementary to the double-stranded target DNA and to which RecA protein is bound, is greatly reduced when an excessive amount of heterologous DNA is present in a given sample. To prevent this reduction in reaction efficiency, the amount of RecA protein, as well as that of RecA protein-coated homologous probe has to be increased in proportion to the amount of the total DNA in the sample (Rigas B. et al., Proc. Natl. Acad. Sci. USA, 83: 9591–9595 (1986)).

However, an increase in the amount of RecA protein-coated homologous probe in proportion to the total amount of DNA in a given sample increases the amount of the RecA protein/homologous probe/target DNA/heterologous DNA complex, which correspondingly increases the final amount of heterologous DNA contaminating the double-stranded target DNA recovered from the sample. Such contamination reduces the specificity of the reaction. Therefore, it seems a problem that in isolating double-stranded target DNA, the amount of the contaminating heterologous DNA recovered together with double-stranded target DNA is dependent on the amount of the homologous probe used in the reaction. This problem is especially significant if the ratio of target DNA to heterologous DNA is less than 1:1,000.

The heterologous DNA may be removed from the complex by utilizing the differences in sodium chloride or $Mg^{2+}$ sensitivity between the probe/target DNA and the probe/heterologous DNA complexes (Honigberg S. M. et al., Proc. Natl. Acad. Sci. USA, 83: 9586–9590 (1986); Rigas B. et al., Proc. Nail. Acad. Sci. USA, 83: 9591–9595 (1986); U.S. Pat. No. 4,888,274). It was reported that when one uses a long, circular homologous probe of more than 5,000 nucleotides or a long stretch linear homologous probe of more than 3,000 nucleotides, it seems possible to isolate the double-stranded target DNA contained in a given sample at a ratio of 1 target DNA molecule per about 200 to 1,000 heterologous DNA molecules with certain specificity. The heterologous DNA may be removed from the complex of homologous probe/target DNA by utilizing the difference between the two complexes in sensitivity to sodium chloride or $Mg^{2+}$. The stability of the homologous probe/heterologous DNA complex significantly differs from that of the homologous probe/target DNA complex.

However, when one uses a circular homologous probe containing a comparatively short sequence, e.g., a 700-nucleotide sequence complementary to a portion of the target DNA, the final yield of the double-stranded target DNA is significantly lowered. This is the case even if the concentration of the double-stranded target DNA is relatively high, such as one molecule per 50 molecules in a given sample. (Teintze M. et al., Biochem. Biophys. Res. Comm., 211: 804–811 (1995)). Therefore, when the amount of the double-stranded target DNA present in the DNA sample is extremely small (for example, at a molar ratio less than 1 molecule/1,000 molecules), it is unclear whether or not one can use a homologous probe to isolate double-stranded target DNA.

It is therefore extremely difficult to selectively eliminate the heterologous DNA from the RecA protein/homologous probe/target DNA/heterologous DNA complex, wherein the amount of heterologous DNA exceeding that of target DNA is more than 1,000-fold in a given sample. Particularly, when the length of the complementary sequence common to both the double-stranded target DNA and the homologous probe (the length of homologous probe) is short, i.e., less than 700 nucleotide sequence, the use of such short probes will make it more difficult for the selective elimination of heterologous DNA. This is because the bond within the homologous probe/target DNA complex, mediated by a short RecA-bound homologous probe, is significantly unstable in comparison with the bond within the same complex, mediated by a long homologous probe consisting of more than 3,000 complementary nucleotide sequence to the whole region of the double-stranded target DNA. Washing under stringent conditions will break the homologous probe/target DNA complex when a short probe is used.

When ATPγS is employed as a co-factor, it is difficult to selectively eliminate only the heterologous DNA from the complex, since the bond within the RecA protein/ homologous probe/heterologous DNA/target DNA complex is extremely stable. Alternatively, it is possible to eliminate RecA proteins from the complex prior to the process of removing the heterologous DNA from it. However, the stability of the homologous probe/target DNA complex without RecA protein distinctively decreases in comparison with that of the RecA protein/homologous probe/target DNA complex. This alternative, therefore, is not preferred. (Teintze M. et al., Biochem. Biophys. Res. Commun., 211: 804–811 (1995)).

Due to the fact that the amount of the contaminating heterologous DNA recovered with double-stranded target DNA is dependent on the amount of the homologous probe used in the reaction, as previously described, reducing the amount of homologous probe in the reaction may facilitate the efficiency of the selective elimination of heterologous DNA. Reducing only the amount of homologous probe, however, will also reduce the efficiency of homologous pairing between a homologous probe and a target DNA.

It has been demonstrated that the efficiency of the reaction, which depends on the length of the complementary sequence common to both the double-stranded target DNA and the homologous probe (the length of homologous probe), decreases as the length of the homologous probe deceases. (Hsieh P. et al., Proc. Natl. Acad. Sci. USA, 89: 6492 (1992); Sena E. P., Nature Genetics, 3: 365–372 (1993); Jayasena V. K. et al., J. Mol. Biol., 230:1015 (1993), etc.). Particularly, the efficiency of the homologous pairing is remarkably reduced when a homologous probe of less than several hundred nucleotide sequence is used in the reaction. Accordingly, it is extremely difficult to detect and/or isolate double-stranded target DNA efficiently by using a short homologous probe alone, particularly, when the amount of heterologous DNA existing in a given sample is more than 1,000-fold amount of target DNA.

It was reported that when one uses a long circular homologous probe of more than 5,000 nucleotides in homologous pairing between the homologous probe and a target DNA, contained at a ratio of one target DNA molecule to 1,000 heterologous DNA molecules in a sample, the reaction efficiency will be reduced when the amount of the RecA-coated homologous probe is reduced. The reduction of the reaction efficiency of homologous pairing, however, was suppressed by adding a long circular heterologous probe of more than 6,000 nucleotides to the pairing reaction at the ratio of less than sevenfold (molar ratio) of the amount of the homologous probe (Honigberg S. M. et al., Proc. Natl. Acad. Sci. USA, 83: 9586–9590 (1986)).

Therefore, a need exists to improve the efficiency and the specificity of the reaction of the conventional methods using a recombinase such as RecA protein for targeting, enriching, detecting and/or isolating an extremely small amount of double-stranded target DNA present in a given DNA sample (tar example, at a molar ratio of less than one molecule to 1,000 molecules) (M. Teintze et al, Biochem. Biophys. Res. Comm., 211, 804–811 (1995)). A need also exists for employing a short-strand homologous probe for various applications as discussed above.

SUMMARY OF THE INVENTION

It is therefore an object of the present invention to provide a method utilizing RecA-like recombinase for targeting, enriching, detecting, and/or isolating a target nucleic acid sequence with high efficiency and specificity. It is also an objective of the present invention to provide a RecA-like recombinase mediated method utilizing a short-strand probe for targeting., enriching, detecting, and/or isolating a low level target nucleic acid sequence in a given sample.

These and other objects and advantages are achieved by using a method of the present invention utilizing RecA-like recombinase for targeting, enriching, detecting and/or isolating a double-stranded nucleic acid target sequence in a sample. The method comprises the steps of providing a RecA-like recombinase, a homologous nucleic acid probe, a heterologous nucleic acid probe; and mixing the RecA-like recombinase, the homologous nucleic acid probe, the heterologous nucleic acid probe with the double-stranded target nucleic acid sequence in the sample, wherein the specificity of the homologous paring and/or strand exchange between the double-stranded nucleic acid target sequence and the homologous nucleic acid probe is increased due to the addition of the heterologous nucleic acid probe.

The methods in accordance with the present invention have been found to provide a number of advantages. As explained in greater detail below, it has been found that the present invention makes it possible to target, enrich, detect, and/or isolate a low-level target nucleic acid sequence contained in a given sample with high efficiency and specificity. The present invention also makes it possible to use a short homologous probe to detect a target sequence having only partial sequence been revealed.

The methods in accordance with the present invention are well suited for use in isolation and subsequent cloning of a target gene from a mixture of cDNAs or genomic DNAs. They are also well suited for use in screening of the target gene from various gene libraries, particularly, isolating and screening of the target gene whose nucleotide sequence or amino acid sequence is only partially revealed.

The methods of the present invention may also be used in the amplification of the target DNA sequence using RecA-like recombinase; mapping of various genes, such as RARE-based mapping using an oligonucleotide probe; nucleotide sequence specific modification or cleavage of the target DNA using an oligonucleotide.

Furthermore, the methods of the present invention may be used in in-situ hybridization methods using RecA-like recombinase to improve the specificity or the efficiency of the hybridization. They may also be used as a gene therapy technique by means of gene alternation or transcription inhibition using in vivo gene-targeting in living cells.

In this use of the method in accordance with the present invention, homologous pairing and/or strand exchange between a homologous probe and a target sequence, mediated by RecA-like recombinase, occurs in the presence of a RecA-like recombinase coated heterologous probe. In an embodiment of the present invention, the weight ratio of the amount of homologous probe to the amount of heterologous probe is between about 1:1 to 1:500.

The invention is defined in its fullest scope in the appended claims and is described below in its preferred embodiments.

DETAILED DESCRIPTION OF THE INVENTION

The present invention is based on a surprise discovery that the addition of a heterologous probe to a RecA-like recombinase mediated reaction system increases the specificity of homologous pairing and/or strand exchange between a target DNA and a homologous probe complimentary to the target DNA, particularly, when a short homologous probe is used.

In addition, it is a surprise discovery of the present invention that reducing the amount of a homologous probe and adding a heterologous probe instead into a RecA-like recombinase mediated reaction system provide a higher specificity than that obtained when the homologous probe is used alone. This is also true even when a short linear homologous probe of less than several hundred nucleotides in length is used in the presence of at least 1,000-fold excess of heterologous DNA over the target DNA in a given sample.

Accordingly, the present invention provides a method for targeting, enriching detecting and/or isolating double-stranded nucleic acid target sequence in a sample by using RecA-like recombinase. The method comprises the steps of providing a RecA-like recombinase, a homologous nucleic acid probe, a heterologous nucleic acid probe; and mixing the RecA-like recombinase, the homologous nucleic acid probe, the heterologous nucleic acid probe with the double-stranded target nucleic acid sequence in the sample, wherein the specificity of the homologous pairing and/or strand exchange between the double-stranded target nucleic acid sequence and the homologous nucleic acid probe is increased due to the addition of the heterologous nucleic acid probe.

For the purpose of the present invention, the "efficiency" is determined based on the amount of a target nucleic acid sequence that is targeted, enriched, detected, or isolated. The "specificity" is determined based on the ratio of the amount of the target nucleic acid sequence that is targeted, enriched, detected, or isolated and the total amount of the target nucleic acid sequence plus the heterologous nucleic acid sequence that is targeted, enriched, detected, or isolated.

RecA-like recombinases utilized in the present invention include recombinases which have catalytic activity similar to of RecA protein derived from *Escherichia coli*. RecA protein can mediate both homologous pairing and/or strand exchange between appropriate DNA molecules in in vitro homologous recombination assays (Kowalczykowski,S., *Ann. Rev. Biohpys. Biophysical Chem.*, 20:539–575 (1991), Radding C., M., *Biochem. Biophys. Acta* 1008:131–139 (1989), Radding C., M., *J. Biol. Chem.* 266:5355–5358 (1991); also see Golub, E., et al., *Nucleic Acids Res.* 20:3121–3125 (1992)). In addition to DNA-DNA hybridization, RecA protein can promote RNA-DNA hybridization. For example, RecA protein coated single stranded DNA can recognize complimentarity with naked RNA (Kirkpatrick, S. et al., *Nucleic Acids Res.* 20:4339–4346 (1992)). Therefore, any recombinase which can promote both homologous pairing and/or strand exchange between appropriate DNA molecules or between DNA and RNA molecules may be used in the present invention.

RecA-like recombinases have been isolated and purified from many prokaryotes and eukaryotes. The examples of such recombinases include, but are not limited to, the wild type RecA protein derived from *Escherichia coli* (Shibata T. et al., Method in Enzymology, 100:197 (1983)), and mutant types of the RecA protein (e.g., RecA 803: Madiraju M. et al., Proc. Natl. Acad. Sci. USA, 85: 6592 (1988); RecA 441(Kawashima H. et al., Mol. Gen. Genet., 193: 288 (1984), etc.); uvsX protein, a T4 phage-derived analogue of the protein (Yonesaki T. et al., Eur. J. Biochem., 148: 127 (1985)); RecA protein derived from Bacillus subtilis (Lovett C. M. et al., J. Biol. Chem., 260: 3305 (1985)); Recl protein derived from Ustilago (Kmiec E. B. et al., Cell, 29 :367 (1982)); RecA-like protein derived from heat-resistant bacteria (such as Thermus aquaticus or Thermus thermophilus ) (Angov E. et al., J. Bacteriol., 176: 1405 (1994); Kato R. et al., J. Biochem., 114: 926 (1993)); and RecA-like protein derived from yeast, mouse and human (Shinohara A. et al., Nature Genetics, 4: 239 (1993)).

In a preferred embodiment, RecA protein isolated and purified from a culture of *Escherichia coli* may be used. (E., Kuramitsu S. et al., J. Biochem., 90: 1033 (1981); Shibata T. et al., Methods in Enzymology, 100: 197 (1983)). Commercially available RecA protein may also be used (Boehringer-Mannheim, Pharmacia).

As used herein, the term "nucleic acid" encompasses RNA as well as DNA and cDNA. In the present invention, there is no specific restriction on a double-stranded nucleic acid target sequence for its length, type, or shape. For example, the double-stranded nucleic acid target sequence may be in a circular form or a linear form.

Preferably, the double-stranded nucleic acid target sequence is double-stranded target DNA. The double-stranded target DNA may be, but is not limited to, genomic DNA, cDNA derived from prokaryotes and eukaryotes, DNA derived from viruses or bacteriophages, fragments of such genomic DNA or cDNA, and various species of such DNA contained in various kinds of DNA libraries.

A double-stranded nucleic acid target sequence of the present invention may be a nucleic acid sequence contained in a solution; in fixed cells, cellular structures, and intercellular structures; or in living cells or cellular structures which are not fixed. Examples of cells, cellular structures and intercellular structures include, but are not limited to, bacteria, viruses, cellular organs such as nucleus, mitochondria, or chromosome, and parasites such as viruses or bacteria existing in biological samples such as blood. Cells or cellular structures may be fixed by means of conventional methods using organic solvents (e.g., methanol, ethanol etc.), acids (e.g., acetic acid) or cross-linking agents (e.g., formialin, paraformaldehyde). Those methods of fixing are well within the skill of the art in view of the instant disclosure.

A double-stranded nucleic acid target sequence of the present invention, if desired, may be labeled using conventional methods well known in the art. The target sequence may be labeled by, but not limited to, radio isotopes (e.g., $^{32}P$, $^{35}S$, etc.), fluorescent pigments (e.g., FITC, rhodamine etc.), enzyme labels (e.g., peroxidase, alkaline phosphatase etc.), chemiluminescent agents (e.g., acridinium ester etc.), and a various sorts of labels and ligands such as biotin or digoxigenin. Those labeling methods are well known to a person skilled in the art in view of the instant disclosure.

It should be understood that, although the methods in accordance with the present invention are primarily directed to the targeting, enriching, detecting, and/or isolating of double-stranded target DNA, they may also be used for other duplex nucleic acid target sequences. Examples of such duplex nucleic acid target sequences include, but are not limited to, DNA/RNA sequences or possibly double-stranded RNA elements, double-stranded or single-stranded nucleic acid sequences associated with viral, bacterial or parasitic pathogens.

As used herein, the term "single-stranded nucleic acid probe" means single-stranded nucleic acids. The term "nucleic acid" encompasses RNA as well as DNA and cDNA. Preferably, single-stranded DNA is employed. There is no restriction regarding the shape of a probe, and thus either a circular form or a linear form may be used.

Commercially available products of single-stranded or double-stranded nucleic acid sequences can be used as probes of the present invention. Probes can also be prepared using the methods well-known in the art. For example, probes may be prepared directly from viruses, bacteriophages, plasmids, cosmids, or other vectors which have a target sequence, by means of, e.g., a nick-translation method and random prime method or the like. If desired, a probe can be prepared by restriction digest of the segment corresponding to the probe from the vector and followed by electrophoretic isolation of the specific restriction fragment, or by amplification of the probe sequence using the PCR method. Although the probe thus obtained is usually double-stranded, if desired, a single-stranded probe can be obtained by denaturing or by sub-cloning of the double-stranded sequence into a single-stranded vector such as M13 phage. Alternatively, a single-stranded probe can be prepared by oligo-nucleotide synthetic methods. A long probe can be prepared by joining sub-fragments of the probe after the synthesis of those sub-fragments.

A homologous probe in accordance with the present invention is a nucleic acid probe which has a region of homology with a selected base sequence in a duplex nucleic acid target sequence. Preferably, a homologous probe is a single-stranded DNA probe. As used herein, the term probe "homology" with the target means that the single-stranded probe and target duplex have a region of similar or exact base pair sequence which allows the probe to recognize and hybridize with the corresponding base pair region in the duplex target. The extent of base pair mismatching which is allowed without losing homology may be as high as 20% to 30%, depending on the distribution and lengths of mismatched base pairs. In a preferred embodiment, the homologous probe is single-stranded nucleic acid which contains the sequence having at least more than 70% homology to the partial or whole sequence of a target nucleic acid. In order to ensure sequence specific homologous pairing (hybridization reaction) between the double-stranded nucleic acid target sequence and the homologous probe, it is preferable that the homologous probe generally contains the sequence that is at least 90–95% homologous to the partial or whole sequence of the double-stranded nucleic acid target sequence.

A homologous probe in accordance with the present invention may be prepared by denaturing a double-stranded nucleic acid probe which is complementary to either one or both strands of a target sequence. The homologous probe may also contain an extended terminal portion which is not complementary to any of the nucleic acid strands in the sample. When both strands of a double-stranded homologous probe have such extended sequences at their termini, the extended sequences may be complementary to each other.

A homologous probe in accordance with the present invention is at least 15 nucleic acid residues in length, and preferably 15–2,000 nucleic acid residues in length. A longer polynucleotide probe (more than 2,000 nucleic acid in length) may also be used (Hsieh P. et al., Proc. Natl. Acad. Sci. USA, 89:6492 (1992)). Preferably, the length of required homology between a probe and a target is at least about 15 base pairs.

If desired, a homologous probe may be labeled for detection and/or isolation using conventional methods known in the art. Examples of the labels that may be used to label a homologous probe include, but are not limited to, radio isotopes (e.g., $^{32}P$, $^{35}S$ etc.), fluorescent pigments (e.g., FITC, rhodamine etc.), enzyme labels (e.g., peroxidase, alkaline phosphatase etc.), chemiluminescent agents (e.g., acridinium ester etc.), and a various sorts of labels and ligands such as biotin or digoxigenin.

In the present invention, at least one species of the homologous probes is used in combination with at least one species of RecA-like recombinase. For example, a homologous probe may be coated with RecA-like recombinase to form a homologous probe/RecA-like recombinase complex using a method that is well known in the art. The amount of homologous probe to be used in a sample is usually 0.1–200 ng, preferably 0.5–150 ng, when the sample contains about 1 $\mu$g of DNA (target DNA and heterologous DNA).

The heterologous probe employed in the present invention is a nucleic acid probe which is not sufficiently complementary to the target sequence. A heterologous probe is not sufficiently complementary to a target sequence if it cannot hybridize with the target sequence nor form a stable heterologous probe/target sequence complex. In a preferred embodiment, the sequence of the heterologous probe may show low complementarity to a sequence other than the target sequence in a target molecule comprising the target sequence and a vector sequence. For example, it may show low complementarity to a vector sequence, in which the target sequence is integrated or is used for constructing the gene library. However, it is preferred that such complementarity should be sufficiently low such that a heterologous probe/target molecule complex or a heterologous probe/vector sequence complex would not be formed.

The heterologous probe may be a DNA probe as well as an RNA probe. Preferably, the heterologous probe is single-stranded DNA. There is no restriction regarding the shape of a probe, and thus either a circular form or a linear form can be used. The probe may be prepared by denaturing the double-stranded heterologous probe.

For example, if the DNA sample is derived from a human, the heterologous probe used in the system may be a single-stranded nucleic acid probe derived from, but not limited to, a virus or bacteriophage, preferably, single-stranded phage DNA such as M13 or ø X174, or single-stranded DNA generated from the fragment of lambda phage DNA; a single-stranded nucleic acid probe derived from microorganisms, such as RNA derived from *Escherichia coli* or yeast; a single-stranded nucleic acid probe derived from eukaryotes except humans, such as single-stranded DNA generated from DNA fragments from salmon sperm.

Preferably, the heterologous probe employed in the present invention does not contain any labels or ligands.

The heterologous probe used in the present invention is at least 15 nucleic acid residues in length. Preferably it is about 15–20,000 nucleic acid residues in length, and more preferably 60–10,000 nucleic acid in length. A longer polynucleotide probe, such as a probe of more than 20,000 nucleic acid residues in length, may also be used.

In the present invention, at least one species of heterologous probes is used in combination with at least one species of recombinase. For example, a heterologous probe of the present invention may be coated with RecA-like recombinase to form a heterologous probe/RecA-like recombinase complex under reaction conditions well known in the art. The amount of a heterologous probe to be used in a sample is usually 0.1–500 ng, preferably 20–250 ng, when the sample contains about 1 $\mu$g of DNA (target DNA and heterologous DNA).

In the present invention, co-factors may be added to the reaction system in association with the recombinase used. For example, when RecA protein derived from *Escherichia coli* is used as a recombinase, RecA protein can be bound to the homologous probe and the heterologous probe, according to the conventional method well known in the art, in the presence of co-factors. Examples of such co-factors include, but are not limited to, rATP, alone or in the presence of an rATP regeneration system, (for example, rATP regeneration system manufactured by Boehringer-Mannheim GmbH), ATPγS, GTPγS, dATP, a mixture of ATPγS and ADP, a mixture of ADP and $AlF_4^-$ (aluminium nitrate and sodium fluoride), a mixture of dADP and $AlF_4^-$, a mixture of ATP and $AlF_4^-$, and a mixture of dATP and $AlF_4^-$ (Rigas B. et al., Proc. Natl. Acad. Sci. USA, 83: 9591–9595 (1986); Hsieh P. et al., Proc. Natl. Acad. Sci. USA, 89: 6492–6496 (1992); Ferrin L. J. et al., Science, 254: 1494–1497 (1991) Sena E. P., Nature Genetics, 3: 365–372 (1993): Teintze M. et al., Biochem. Biophys. Res. Commun., 211: 804–811 (1995); Jayasena V. K. et al., J. Mol. Biol., 230: 1015 (1993); Kowalczykowski S. (C. et al., Proc. Natl. Acad. Sci. USA, 92: 3478–3482 (1995); Moreus P. L. et al., J. Biol. Chem., 264: 2302–2306 (1989); U.S. Pat. No. 4,888,274, WO93/05177, WO93/05178, WO95/18236, WO93/22443 etc.). Preferably, co-factors are ATP (preferably, 1–5 mM), GTPγS (preferably, 0.05–5 mM), ATPγS (preferably, 0.01–3 mM), a mixture of ATPγS and ADP (0.3–3 mM ATPγS+) 0.3–1.1 mM ADP), or a mixture of ADP and $AlF_4^-$ [0.02–5 mM ADP+0.01–0.5 mM $Al(NO_3)_3$+5–50 mM NaF].

The homologous probe and the heterologous probe in accordance with the present invention may be used in either a single-stranded or a double-stranded form. In general, the probe is subjected to denaturation by heating for about 5 minutes at 95–100° C. prior to the reaction, and after chilling the probe on ice for about 20 seconds to 1 minute, the probe is used for the binding reaction with RecA-like recombinase. If desired, the probe is centrifuged for about 1–10 seconds at 0–4° C. prior to the binding reaction with the recombinase. Though the denatured single-stranded probe can be stored in a freezer at −20° C., preferably, it is immediately mixed with the standard reaction solution containing a co-factor and a RecA-like recombinase in an ice water bath. The single-stranded probe is bound to the RecA-like recombinase by incubating the mixed solution at 37° C. for 0–20 minutes (pre-incubation is not always necessary if ATP, GTPγS, ATPγS or a mixture of ATPγS and ADP is used as a co-factor). In this reaction, RecA-like recombinase generally binds to the single-stranded probe at the ratio of one molecule to about 3 nucleotides of a single-stranded probe. The binding reaction can be carried out at the mixing ratio of the amount of RecA protein (monomer) to nucleotides of the probe ranging from 5:1 to 1:8, preferably from 3:1 to 1:6. If desired, the reaction is performed in the presence of single-strand DNA binding protein (SSB), topoisomeraseI or topoisomeraseII.

The homologous probe of the present invention may be used as a labeled homologous probe, when it is bound to RecA-like recombinase having various labels or ligands described in the reference WO95/18236, the text of which is incorporated herein by reference. On the contrary, it is not preferable to use the heterologous probe with RecA-like recombinase having various labels or ligands.

The homologous probe/RecA-like recombinase complex and the heterologous probe/RecA-like recombinase complex are added to the DNA sample under conditions for avoiding the denaturation of the double-stranded target DNA, for example, at a temperature lower than that for melting double-stranded DNA. The mixture is incubated at 37° C. for generally 10 minutes-24 hours, preferably 15 minutes-2 hours to carry out homologous pairing (hybridization).

The ratio of the amount of homologous probe to that of the heterologous probe added to the reaction is generally 1:1–1:500, preferably 1:1–1:250. It is a surprise discovery of the present invention that the use of the heterologous probe together with the homologous probe in a ratio as described above greatly increases the specificity of targeting, enriching, detecting and isolating of a target nucleic acid sequence. As described in the Examples of the present invention, for example, the method of the present invention is applied to isolate double-stranded target DNA from a sample containing about 1 [g of total DNA with a molar ratio of target DNA to non-target DNA being 1:10,000. When 200 ng of RecA protein coated homologous probe of 60–275 nucleotide length is used alone, the specificity of the reaction is extremely low. A large amount of heterologous DNA other than target DNA is recovered in contamination with the double-stranded target DNA, though, a certain amount of the double-stranded target DNA is also recovered. When the amount of the RecA protein coated homologous probe is reduced to 50 ng and used alone, the efficiency of the reaction decreases in comparison with the efficiency of the reaction wherein 200 ng of homologous probe is used alone, and likewise the yield of the double-stranded target DNA decreases. However, when 50 ng of the RecA protein coated homologous probe is reacted with the sample DNA in the presence of 150 ng of the RecA protein coated heterologous probe, not only the reaction efficiency is increased and a larger amount of the double-stranded target DNA is recovered in comparison with the reaction wherein 200 ng of homologous probe is used alone, but also the specificity of the reaction greatly increases because of the strong inhibition of the recovery of heterologous DNA. When the amount of the homologous probe is further reduced (25 ng or 10 ng), and thus the ratio of the homologous probe to the heterologous probe is further reduced (homologous probe: heterologous probe=10:190, or homologous probe: heterologous probe=25:175), the specificity of the reaction is further distinctively improved.

It should be understood that the ratio of the amount of homologous probe to that of heterologous probe, also the ratio of RecA-like recombinase bound to the probes may be altered by considering the property of the sample and the like. In view the teaching of this disclosure, one skilled in the art can alter the ratio in light of the changes in the property of the sample without undue experiments.

In an embodiment of the present invention, the reaction solution for the homologous pairing (hybridization) may be prepared so that the final concentration of each component may be within the range as follows: 1–100 mM Tris-HCl buffer or Tris-acetate buffer, 1–30 mM magnesium acetate or magnesium chloride, 0–50 mM sodium acetate or sodium chloride, 0–3 mM dithiothreitol, 0–100 mM EGTA, 0–50 mM spermidine, 0–10% glycerol, 1–5 mM ATP or 0.05–5 mM GTPγS or 0.01–3 mM ATPγS or 0.3–3 mM ATPγS+ 0.3–1.1 mM ADP, 0.002–0.025 mM RecA protein, 0.5–150 ng of homologous probe and 20–200 ng of the heterologous probe per reaction, and about 1 lg of the DNA sample (target DNA+heterologous DNA).

The methods of the present invention may be used in connection with well-known methods in the art (U.S. Pat. No. 4,888,274, WO093/05177, WO093/05178, WO095/18236, Teintze M. et al., Biochem. Biophys. Res. Commun., 211: 804–811 (1995)) for detection or isolation of a complex formed between double-stranded target DNA and RecA protein coated homologous probe, wherein either the double-stranded target DNA, or RecA protein, or the homologous probe may be labeled with labels or ligands. For example, the complex may be a complex of homologous probe carrying various labels or ligands/RecA protein/ double-stranded target DNA, or a complex of homologous probe/RecA protein carrying various labels or ligands/ double-stranded target DNA, or a complex of homologous probe/RccA protein/double-stranded target DNA carrying various labels or ligands. In accordance with the present invention, those complexes are formed by homologous pairing (hybridization reaction) using RecA-like recombinase in the presence of both a homologous probe and a heterologous probe.

In a preferred embodiment, a method for isolating double-stranded target DNA comprises the steps of: labeling the homologous probe with biotin; coating the homologous probe and a non-labeled heterologous probe with RecA protein in the presence of an appropriate co-factor (for example, GTPγS or a mixture of ATPγS and ADP); reacting the RecA coated homologous and heterologous probes with a DNA sample containing double-stranded target DNA to form a complex of homologous probe/target DNA; and then capturing the complex on magnetic beads (BioMag, Dynal) conjugated with streptavidin. After washing out the DNA and probes which are not captured on the beads, biotin-labeled homologous probe/double-stranded target DNA complex bound to the beads is incubated in a solution containing NaCl at a temperature between the room temperature and 85° C. for about 5–15 minutes to separate (elute) the double-stranded target DNA fraction from the beads. Preferably, the recovered target DNA fraction is then used to transform appropriate host cells, followed by selecting the transformed cells having the target DNA, and recovering the target DNA from the transformed cells.

To carry out the methods described above, the present invention also provides a kit for targeting, enriching, detection and/or isolation of a double-stranded target nucleic acid sequence in a sample. The kit may comprise a carrier means being compartmentalized to receive in close confinement one or more container means such as vials, tubes, and the like, each of the container means comprising one of the separate elements to be used in the methods of the present invention.

For example, one of the container means may contain RecA-like recombinase. A second container may contain a solid phase designed to capture the complex of double-stranded target nucleic acid sequence and homologous probe labeled with markers or ligands. Containers are also provided for containing co-factors, heterologous probe and washing solution separately.

In an embodiment of the present invention, a kit in accordance with the present invention may comprise the following elements in separate compartments respectively: RecA-like recombinase, appropriate co-factors, a heterologous probe, a solid phase designed to capture the complex of double-stranded target DNA and homologous probe labeled with marker or ligand, and washing solution.

The method in accordance with the present invention may be used to target, enrich, detect and/or isolate with high specificity target nucleic acid molecules existing in a given sample at a very low level. In an embodiment of the present invention, the molar ratio of the target nucleic acid molecules to the non-target nucleic acid molecules may be less than 1:1,000. Preferably, the ratio may be more than 1:1, 000,000, and more preferably more than 1:500,000.

The methods of the present invention are well suited for use in isolation and subsequent cloning of the target gene from a mixture of cDNAs or genomic DNAs as well as in screening for the target gene from various gene libraries. Examples of such gene libraries include, but are not limited to, DNA libraries, cosmid libraries, YAC libraries, and the like. Since a short strand probe may be used in the present invention, it becomes possible to isolate or screen a target gene whose nucleic acid sequence or amino acid sequence is only partially revealed.

The present invention may also be used in conjunction with well-known methods in the art for the following purposes: amplification of the target DNA sequence using RecA-like recombinase (U.S. Pat. No. 5,223,414, WO91/ 17267); mapping of various genes, such as RARE (RecA-Assisted Restriction Endonuclease cleavage) based mapping using an oligonucleotide probe (Ferrin L. J. et al., Nature Genetics, 6:379 (1994); Revet B. M. et al., J. Mol. Biol., 232:779 (1993)); nucleotide sequence-specific modification (methylation or alkylation) or cleavage of the target DNA using oligonucleotide (Koob M. et al., Nucleic Acid Res., 20:5831 (1992); Golub E. I. et al., Nucleic Acid Res., 20:3121 (1992); Mikhail A. et al., Biochemistry, 34:13098 (1995)). Applications of the present invention in conjunction with the above-known methods are well within the skill in the art in view of the instant disclosure.

Furthermore, the present invention may be used for isolation and/or detection of the specific target DNA of interest from clinical specimens containing a mixture of cDNA or genomic DNA. Therefore, the present invention allows the diagnosis of a variety of genetic aberration or mutation, or infectious diseases caused by a variety of pathogenic microorganism or viruses.

Moreover, the present invention may also be used in conjunction with an in-situ hybridization method, mediated by RecA-like recombinase (WO93/05177, WO095/18236), to improve the specificity or the efficiency of the hybridization. It is also applicable as a gene therapy technique and a transgenic technique to produce transgenic animals or plants by means of gene alternation or transcription inhibition using in vivo gene-targeting in the living cells (U.S. Pat. No. 5.468,629, WO093/2244; Golub E. I. et al., Nucleic Acid Res., 20: 3121 (1992); Golub E. I. et al., Proc. Natl. Acad. Sci. USA, 90; 7186 (1993), etc.). Applications of the present invention in conjunction with the above known methods are well within the skill in the art in view of the instant disclosure.

For example, when the present invention is used for in vivo gene-targeting in living cells, both RecA-like recombinase coated homologous probe and heterologous probe are used in forming the complex of RecA-like recombinase mediated homologous probe and double-stranded target DNA. Accordingly, a method for targeting a double-stranded nucleic acid target sequence in a sample of living cells by in vivo gene targeting method using a RecA-like recombinase may comprise the following steps: (a) providing a recombinase coated homologous probe and a recombinase coated heterologous probe; (b) introducing the homologous probe and the heterologous probe into the living cells; and (c) incubating said living cells for a sufficient period of time to allow the homologous probe to be transformed into the genome of the cells.

The conventional method of in vivo gene-targeting in living cells, which may be used in conjunction with the present invention, is described in U.S. Pat. No. 5,468,629 and WO093/2244, the relevant text of which is incorporated herein in its entirety by reference.

The following are examples provided to describe the present invention. They are intended only for illustrating the present invention and not as limiting the scope of the present invention.

EXAMPLE I

Preparation of Target DNA, Heterologous DNA, Homologous Probe and Heterologous Probe 1. Preparation of the Double-stranded Target DNA and the Heterologous DNA Php53B, a 6.6 kb plasmid containing a complete sequence of cDNA corresponding to the sequence of human tumor suppressor gene p53 (Zakut-Houri R. et al., EMBO J., 4: 1251 (1985)) was used as double-stranded target DNA in a circular form, and plasmid vector pUC18 (2.7 kb) was used as heterologous double-stranded DNA in circular form. These plasmids were purified from the cells of Escherichia coli, accommodating each plasmid, using QIAGEN Plasmid Maxi Kit (manufactured by QIAGEN GmbH).

2. Preparation of the Homologous Probe

The double-stranded DNA fragments of 275 bp (SEQ ID NO:1) and 60 bp (SEQ ID NO:2), which contain the partial sequence of p53 cDNA, were prepared under the standard amplification condition (PCR method) using Taq polymerase and the following primers: 5'-CCTTGCCGTCCCAAGCAATGGATGA-3' (SEQ ID NO:11, and corresponding to the 1–25th nucleotide sequence of the SEQ ID NO:1), 5'-CGTGCAAGTCACAGACTTGGCTGTC-3' (SEQ ID NO:12, and corresponding to the 251–275th nucleotide sequence of the SEQ ID NO:1), 5'-AGCTACGGTTTCCGTCTGGGCTTCT-3' (SEQ ID NO:13, and corresponding to the 1–25th nucleotide sequence of the SEQ ID NO:2), 5'-CGTGCAAGTCACAGACT TGGCTGTC-3' (SEQ ID NO:12, and corresponding to the 36–60th nucleotide sequence. of SEQ ID NO:2). The above primers are biotinylated at their 5'-ends. The double-stranded fragments were used as homologous probes after being denatured into single-stranded DNA by heating immediately before use. The nucleotide sequences corresponding to these regions of p53 cDNA are shown as SEQ ID NOS:1 and 2.

The double-stranded DNA fragments of 410 bp (SEQ ID NO:9), 779 bp (SEQ ID NO:10), and 1,317 bp (SEQ ID NO:8), which contain the partial sequence of p53 cDNA, were also prepared under standard amplification conditions (PCR method) using Taq polymerase and the following primers (manufactured by GENOSYS): 5'-CCTTGCCGTCCCAAGCAATGGATGA-3' (SEQ ID NO:11, and corresponding to the 236–260th nucleotide sequence of the SEQ ID NO:8), 5'-CGTCATGTGCTGTGACTGCTTGTAG-3' (SEQ ID NO:14, and corresponding to the 621–645th nucleotide sequence of the SEQ ID NO:8), 5'-CCTTGCCGTCCCAAGCAATGGATGA-3' (SEQ ID NO:11, and corresponding to the 236–260th nucleotide sequence of the SEQ ID NO:8), 5'-CCCTTTCTTGCGGAGATTCTCTTCC-3' (SEQ ID NO:15, and corresponding to the 990–1,014th nucleotide sequence. of SEQ ID NO:8), 5'-GTCTAGAGCCACCGTCCAGGGAGCA-3' (SEQ ID NO:16, and corresponding to the 1–25th nucleotide sequence of SEQ ID NO:8), and 5'-TCAGTCTGAGTCAGGCCCTTCTGTC-3' (SEQ ID NO:17, and corresponding to the 1,293–1,317th nucleotide sequence of SEQ ID NO:8). The above primers are biotinylated at their 5'-ends. These double-stranded fragments were used as homologous probe after denatured into single-stranded DNA by heating immediately before the use. The nucleotide sequences corresponding to these regions of p53 cDNA are shown as SEQ ID NOS: 9, 10 and 8, respectively.

3. Preparation of the Heterologous Probe

The double-stranded DNA fragments of 500 bp (SEQ ID NO: 3) and 1,393 bp (SEQ ID NO:4), which contain a partial sequence of the genome of lambda phage, were prepared under standard amplification conditions (PCR method) using Taq polymerase and the following primers: 5'-GATGAGTTCGTGTCCGTACAACTGG-3' (SEQ ID NO:18, and corresponding to the 1–25th nucleotide sequence of SEQ ID NO:3), 5'GGTTATC GAAATCAGCC ACAGCGCC-3' (SEQ ID NO:19, and corresponding to the 476–500th nucleotide sequence of SEQ ID NO:3), 5'-GCGGCACGGAGTGGAGCAAGCGTGA-3' (SEQ ID NO:20, and corresponding to the 1–25th nucleotide sequence of SEQ ID NO:4), 5'-ATACGGCTGAGGTTTTCAACGGCCT-3' (SEQ ID NO:21, and corresponding to the 1369–1393th nucleotide sequence of SEQ ID NO:4). The double-stranded fragments were used as heterologous probes after denatured into single-stranded DNA by heating immediately before the use. The nucleotide sequences corresponding to these regions of lambda phage are shown as SEQ ID NOS:3 and 4.

Also, all lambda phage DNA (manufactured by Nippon Gene) are fragmented under the nick-translation reaction in the presence of dNTPs using a commercially available nick-translation kit (manufactured by BRL). The fragments were used as heterologous probes after being denatured into single-stranded DNA by heating immediately before use. ("Lambda DNA fragments" are formed from fragments with 100–1,500 nucleic acid in length).

Salmon sperm DNA (Type III, Sigma) was used as a heterologous probe after it was fragmented and heat-denatured according to conventional methods (Maniatis T. et al., "Molecular Cloning")and then denatured into single-stranded DNA again immediately before the use. Fragments of Salmon sperm DNA have a length of about 100 to 1,500 nucleotides.

Commercially available single strand DNA of M13mp18 (manufactured by New England Biolabs Inc.) was purchased and also used as the heterologous probe.

EXAMPLE 2

Isolation of Double-stranded Target DNA using RecA Protein

1. Target DNA: Heterologous DNA=1:10,000 (when GTPγS was used as a Co-factor)
A. Homologous Pairing (hybridization reaction
(a) preparation of various probe/RecA protein complexes
The double-stranded homologous probes prepared in EXAMPLE 1 2, such as 275 bp, 60 bp, 410 bp, 779 bp, or 1,317 bp sequence, or the mixture of the homologous probes and the various heterologous probes prepared in EXAMPLE 1 3, were diluted in either distilled water or TE buffer (10 mM Tris-HCl, 1 mM EDTA, pH 7.5). The aliquot was transferred to a 0.6 ml microcentrifuge tube and was heated in boiling water for 5 minutes to denature the double-stranded probe. The tube was then rapidly chilled in ice water. 0.9 μl of 10×reaction buffer, [300 mM Tris-HCl (pH 7.5 at 37° C.), 20 mM $MgCl_2$, 4 mM DTT, 30% glycerol], 0.9 μl of 3 mM GTPγS solution, and RecA protein (manufactured by Boehringer-Mannheim GmbH) were added to the tube to form a mixture. The mixture was diluted with distilled water to a total volume of 9 μl and was allowed to react for 12 minutes at 37° C. to allow the formation of probe/RecA complex.

(b) Preparation of probe/target DNA complex

Then 0.9 μl of 10×reaction buffer, 0.9 μl of 3 mM GTPγS solution, 0.9 μl of 0.2 M $MgCl_2$ solution, 245 pg. of php53B, which was double-stranded target DNA in circular form prepared as in EXAMPLE 1.1, and 1 μg of pUC18, which was circular heterologous DNA (molar ratio of target DNA to heterologous DNA is 1:10,000) were mixed and diluted with distilled water to a total volume of 9 μl. This mixture was mixed with either the complex of homologous probe/RecA protein or the mixture of homologous probe/RecA protein complex and heterologous probe/RecA protein complex obtained from the reaction described above. The mixture thus obtained was subjected to the reaction for 60 minutes at 37° C. to allow the hybridization and formation of the complex of probe/target DNA. The type and the amount of the homologous probe, those of the heterologous probe and the amount of RecA protein which were used in each reaction are shown in Table 1. In all reactions, a final volume of the reactant was 18 μl.

B. Capturing/isolation by Magnetic Beads

20 μl of the magnetic beads coated with straptavidin, manufactured by DYNAL®, was transferred to a 0.6 ml microcentrifuge tube and was washed two times in 100μ1 of 33 mM Tris-HCl and 50 mM NaCl (pH7.5) using a Magnetic Beads Separation Rack (MAGNA-SEP™). After discarding the washing solution, the washed magnetic beads were mixed with the whole volume of the hybridization reaction solution obtained above in the 0.6 ml microcentrifuge tube, and this mixture was mixed well and stored for 15 minutes at room temperature with stirring every 2–3 minutes. The magnetic beads were then separated from supernatant using the Magnetic Beads Separation Rack. After discarding the supernatant, magnetic beads were washed twice in 100 μl of 33 mM Tris-HCl and 50 mM NaCl (pH7.5) solution for 5 minutes at 37° C. to get rid of any unbound molecules such as probes, RecA proteins, target DNA and heterologous DNA molecules and the like. After discarding the washing solution, the beads were suspended and mixed with 10 μ of 33 mM Tris-HCl and 200 mM NaCl (pH7.5), and then the mixture was heated to 85° C. for 8 minutes. The supernatant containing target DNA was recovered using the Magnetic Beads Separation Rack.

C. Transformation

100 μl of competent cells, which were prepared from *Escherichia coli* strain JM109 according to the method of Nojima et al. (Inoue H. et al., Gene, 96:23 (1990)), was transferred into a 1.5 ml microcentrifuge tube, and mixed with 2 μl of the supernatant removed from 10 μl of supernatant that recovered in B. This mixture was then stored for 30 minutes on ice. The mixture was subsequently incubated for 30 seconds at 42° C., and then chilled in the ice again for 1–2 minutes. Then 0.5 ml of SOC medium (2% Bacto trypton, 0.5% Bacto yeast extract, 10 mM NaCl, 2.5 mM KCl, 10 mM $MgCl_2$, 10 mM $MgSO_4$, 20 mM glucose) was added to the tube and incubated at 37° C. for 1 hour with shaking. The cells were spread on LB Plate, containing 50–100 μg/ml ampicillin, 1 mg/plate X-gal (5-bromo-4-chloro-3-indolyl-β-D-galactoside), 0.5–1.0 mg/plate IPTG (isopropyl-β-D(-)-thiogalactopyranoside), and incubated over night at 37° C. Under this condition, *Escherichia coli* transformed with php53B, the double-stranded target DNA, shows white colonies, and *Escherichia coli* transformed with pUC18, the heterologous DNA, shows blue colonies.

The various conditions and the results of the transformation obtained under those conditions are shown in Tables 1 and 2.

TABLE 1

Reaction Condition

| No. | Homo. P. Type | Homo. P. Amount | Hetero. P. Type | Hetero. P. Amount | RecA Amount |
|---|---|---|---|---|---|
| 1 | 1,317 bases | 200 ng | — | — | 6.0 μg |
| 2 | 1,317 bases | 67 ng | lambda DNA fragments | 133 ng | 6.0 μg |
| 3 | 779 bases | 200 ng | — | — | 6.0 μg |
| 4 | 779 bases | 100 ng | lambda DNA fragments | 100 ng | 6.0 μg |
| 5 | 779 bases | 67 ng | lambda DNA fragments | 133 ng | 6.0 μg |
| 6 | 779 bases | 20 ng | lambda DNA fragments | 180 ng | 6.0 μg |
| 7 | 410 bases | 200 ng | — | — | 6.0 μg |
| 8 | 410 bases | 100 ng | lambda DNA fragments | 100 ng | 6.0 μg |
| 9 | 410 bases | 67 ng | lambda DNA fragments | 133 ng | 6.0 μg |
| 10 | 410 bases | 10 ng | lambda DNA fragments | 190 ng | 6.0 μg |
| 11 | 275 bases | 200 ng | — | — | 6.0 μg |
| 12 | 275 bases | 50 ng | — | — | 6.0 μg |
| 13 | 275 bases | 50 ng | — | — | 1.5 μg |
| 14 | 275 bases | 133 ng | lambda 500 bases | 67 ng | 6.0 μg |
| 15 | 275 bases | 100 ng | lambda 500 bases | 100 ng | 6.0 μg |
| 16 | 275 bases | 67 ng | lambda 500 bases | 133 ng | 6.0 μg |
| 17 | 275 bases | 50 ng | lambda 500 bases | 150 ng | 6.0 μg |
| 18 | 275 bases | 10 ng | lambda 500 bases | 190 ng | 6.0 μg |
| 19 | 275 bases | 10 ng | lambda 1400 bases | 190 ng | 6.0 μg |
| 20 | 275 bases | 10 ng | salmon sperm DNA | 190 ng | 6.0 μg |
| 21 | 275 bases | 10 ng | M13mp18 | 190 ng | 6.0 μg |
| 22 | 275 bases | 1 ng | lambda DNA fragments | 250 ng | 7.5 μg |
| 23 | 275 bases | 1 ng | lambda DNA fragments | 500 ng | 15.0 μg |
| 24 | 60 bases | 200 ng | — | — | 6.0 μg |
| 25 | 60 bases | 50 ng | — | — | 6.0 μg |
| 26 | 60 bases | 50 ng | — | — | 1.5 μg |
| 27 | 60 bases | 133 ng | lambda 500 bases | 67 ng | 6.0 μg |

TABLE 1-continued

| No. | Homo. P. Type | Homo. P. Amount | Hetero. P. Type | Hetero. P. Amount | RecA Amount |
|---|---|---|---|---|---|
| 28 | 60 bases | 100 ng | lambda 500 bases | 100 ng | 6.0 μg |
| 29 | 60 bases | 67 ng | lambda 500 bases | 133 ng | 6.0 μg |
| 30 | 60 bases | 50 ng | lambda 500 bases | 150 ng | 6.0 μg |
| 31 | 60 bases | 25 ng | lambda 500 bases | 175 ng | 6.0 μg |
| 32 | 60 bases | 25 ng | lambda 1400 bases | 175 ng | 6.0 μg |
| 33 | 60 bases | 25 ng | salmon sperm DNA | 175 ng | 6.0 μg |
| 34 | 60 bases | 25 ng | M13mpl8 | 175 ng | 6.0 μg |
| 35 | 60 bases | 10 ng | lambda 500 bases | 190 ng | 6.0 μg |

As used herein, "homo.p." is a homologous probe; "hetero.p." is a heterologous probe.

All the "lambda DNA fragments" used in table 1 are prepared by a nick-translation of whole lambda phage DNA in the presence of dNTPs using an on-the-shelf nick-translation kit (manufactured by BRL Co., Ltd.)

TABLE 2

The Results of Transformation[1]

| Reaction No. | Number of white colonies | Number of blue colonies | specificity (%)[2] |
|---|---|---|---|
| 1 | 472 | 20,458 | 2.3 |
| 2 | 385 | 861 | 30.9 |
| 3 | 590 | 18,760 | 3.0 |
| 4 | 601 | 1,719 | 25.9 |
| 5 | 499 | 807 | 38.2 |
| 6 | 461 | 330 | 58.3 |
| 7 | 904 | 18,362 | 4.7 |
| 8 | 1,096 | 4,123 | 21.0 |
| 9 | 1,118 | 2,678 | 33.8 |
| 10 | 756 | 252 | 75.0 |
| 11 | 830 | 22,238 | 3.6 |
| 12 | 756 | 11,340 | 6.3 |
| 13 | 406 | 13,036 | 3.0 |
| 14 | 1,540 | 10,380 | 12.9 |
| 15 | 1,626 | 2,254 | 41.9 |
| 16 | 1,488 | 2,357 | 38.7 |
| 17 | 1,744 | 2,688 | 39.4 |
| 18 | 1,224 | 336 | 78.5 |
| 19 | 1,046 | 330 | 76.0 |
| 20 | 1,024 | 270 | 79.1 |
| 21 | 938 | 254 | 78.7 |
| 22 | 543 | 146 | 78.8 |
| 23 | 302 | 199 | 60.3 |
| 24 | 126 | 3,264 | 3.7 |
| 25 | 88 | 3,046 | 2.8 |
| 26 | 6 | 1,020 | 0.6 |
| 27 | 610 | 1,030 | 37.2 |
| 28 | 605 | 786 | 43.5 |
| 29 | 622 | 650 | 48.9 |
| 30 | 604 | 616 | 49.5 |
| 31 | 606 | 270 | 69.2 |
| 32 | 484 | 244 | 66.5 |
| 33 | 646 | 266 | 70.8 |
| 34 | 330 | 320 | 50.8 |
| 35 | 502 | 222 | 69.3 |

[1] Mean values obtained from the three repeated experiments are indicated.
[2] Specificity (%) = number of white colonies ÷ (number of white colonies + number of blue colonies) × 100

The above results show that when a large amount (200 ng) of a homologous probe is used, the reaction specificity is extremely low, although the reaction efficiency is relatively high. As used herein, the reaction specificity is determined based on the number of white colonies versus the total number of white and blue colonies. The reaction efficiency is determined based on the number of white colonies and the amount of target DNA recovered.

For example, when a large amount (200 ng) of a single species of homologous probe, which is longer than 275 nucleotides, was used (see Nos. 1, 3, 7, 11), the reaction efficiency was considered relatively high, since the large number of *Escherichia coli* colonies containing target DNA (the number of white colonies) were observed, and the yield of target DNA was also high. At the same time, however, the number of *Escherichia coli* colonies containing the heterologous DNA (blue colonies) greatly exceeded the number of white colonies, which indicated the reaction specificity was considered to be extremely low.

On the other hand, when a large amount (200 ng) of single species of homologous probe of 60 nucleotide long was used (No.24), not only the specificity of the reaction was extremely low, but also the efficiency of the reaction was significantly lower. The specificity of the reaction is low due to the high level of contamination of the heterologous DNA. The efficiency of the reaction is lower since the yield of the target DNA was greatly reduced in comparison with the yield of the target DNA when the homologous probe of 275 nucleotide was used. When the amount of the homologous probe or RecA protein was reduced (Nos. 12, 13, 25, 26), the contamination of the heterologous probe was slightly inhibited, and the yield of the target DNA also decreased. Subsequently, both the reaction efficiency and the specificity were greatly reduced.

However, when a small amount of the homologous probe (50 ng) was used with a large amount (150 ng) of the heterologous probe (No. 17, 30) in the reaction, the specificity of the reaction was improved. This is due to the inhibition of contamination of the heterologous DNA. When the amount of the homologous probe was further reduced (10 ng of the homologous probe of 275 nucleotides in length, 25 ng or 10 ng of homologous probe of 60 nucleotides in length), and the amount of the heterologous probe was further increased (175 ng or 190 ng) (Nos. 18–21, 31–35), the level of contamination of the heterologous DNA was dramatically reduced in comparison to Nos. 17 and 30, and thus the specificity of the reaction was remarkably improved.

When a reduced amount of the homologous probe (10–133 ng) was used with a large amount (67–190 ng) of the heterologous probe in the reaction (Nos. 8, 9, 14–21, 27–35), the yield of the target DNA was dramatically increased, and therefore, the reaction efficiency itself was considered to be improved. When a short homologous probe such as a probe of 60–410 nucleotide long (the length of a complementary region between target DNA and probe is short) was used in combination with various species of heterologous probes, it was shown that not only the reduction of the reaction efficiency, resulting from using a reduced amount of homologous probe alone, was recovered, but also the reaction efficiency was improved when compared to the efficiency achieved by using an unreduced amount of homologous probe alone.

The above results show that when the heterologous probe that is 1–500 fold of the amount of homologous probe is used (Nos. 2, 4–6, 8–10, 15–23, 28–35), the specificity of the reaction is substantially improved. The specificity is improved more than four times as compared with those obtained when single species of the homologous probe is used without adding the heterologous probe.

2. Target DNA: Heterologous DNA=1:100,000
(GTPγS was used as a co-factor)

A. Preparation of the Heterologous Probe

In addition to the 500 bp fragments of the double-stranded DNA prepared in EXAMPLE 1.3, containing the partial sequence of the genome of lambda phage and salmon sperm DNA, 308 bp of the double-stranded fragments (SEQ ID NO:5), containing the partial sequence of lambda phage, was newly prepared under standard amplification conditions (PCR method) using a primer, 5'-AGGTGCGGTGATACGTGGTGTTTTT -3' (SEQ ID NO:22, and corresponding to the 1–25th nucleotide sequence of SEQ ID NO: 5), another primer, 5'-ATACGGCTGAGGTTTTCAACGGCCT -3' (SEQ ID NO:21, and corresponding to the 284–308th nucleotide sequence of SEQ ID NO: 5), and Taq polymerase. This fragment was used as a heterologous probe after being denatured into single-stranded DNA by heating immediately before the use. The DNA sequence of the fragment is set forth in SEQ ID NO:5.

B. Homologous Pairing (hybridization reaction)

(a) the preparation of various probe/RecA protein complex

The double-stranded homologous probe consisting of 275 bp or 60 bp sequence prepared in EXAMPLE 1.2, containing a partial sequence of p53 cDNA and biotinylated at its 5'-end, or the mixture of the said homologous probe and the various heterologous probes described in EXAMPLE 2.2. A was diluted in either distilled water or TE buffer (10 mM Tris-HCl, 1 mM EDTA, pH 7.5). The aliquot was transferred to a 0.6 ml microcentrifuge tube and was heated in the boiling water for 5 min to denature the double-stranded probe. The lube was rapidly chilled in ice water, then 0.9 μl of 10×reaction buffer [300 mM Tris-HCl (pH 7.5 at 37° C.), 20 mM MgCl$_2$, 4 mM DTT, 30% glycerol], 0.9 μl of 5 mM GTPγS solution, and RecA protein (manufactured by Boehringer-Mannheim GmbH) were added to the tube. The mixture was allowed to react for 12 minutes at 37° C. after dilution with distilled water to a total volume of 9 μl.

(b) The preparation of probe/target DNA complex

Then 0.9 μl of 10×reaction buffer, 0.9 μl of 5 mM GTPγS solution, 0.9 μl of 0.2 M MgCl$_2$ solution, 24.5 pg of php53B which was double-stranded target DNA in circular form prepared as in EXAMPLE 1.1, and 1 μg of pUC18 which was circular heterologous DNA (molar ratio of target DNA to heterologous DNA is 1:100,000) were mixed and diluted with distilled water to a total volume of 9 μl. This mixture was mixed with either the complex consisting of homologous probe and RecA protein or the mixture of homologous probe/RecA protein complex and heterologous probe/RecA protein complex obtained from the reaction described above, and the mixture thus obtained was subjected to the reaction for 60 minutes at 37° C. The type and the amount of the homologous probe, those of the heterologous probe and the amount of RecA protein which were used in each reaction are shown in Table 3. In all the reactions, a final volume of the reactant was 18 μl.

C. Capturing/isolation by Magnetic Beads

20 μl of the magnetic beads coated with straptavidin, manufactured by DYNAL®, were transferred to a 0.6 ml microcentrifuge tube and were washed two times in 100 μl of 33 mM Tris-HCl and 50 mM NaCl (pH7.5) using Magnetic Beads Separation Rack (MAGNA-SEP™). After discarding the washing solution, the washed magnetic beads were mixed with the whole volume of the hybridization-reaction solution obtained above in the 0.6 ml microcentrifuge tube, and this mixture was mixed well and stored for 15 minutes at room temperature with stirring every 2–3 minutes. The magnetic beads were then separated from the supernatant using the Magnetic Beads Separation Rack. After discarding the supernatant, the magnetic beads were washed twice in 100 μl of 33 mM Tris-HCl and 50 mM NaCl (pH7.5) solution for 5 minutes at 37° C. to get rid of any unbounded molecules such as probes, RecA proteins, target DNA, heterologous DNA etc. After discarding the washing solution, the beads were suspended and mixed with 10 μl of 33 mM Tris-HCl and 200 mM NaCl (pH7.5), and then the mixture was heated to 85° C. for 8 minutes. The supernatant containing target DNA was recovered using Magnetic Beads Separation Rack.

D. Transformation

100 μl of competent cells, which were prepared from Escherichia coli strain JM109 according to the method of Nojima et al. (Inoue H. et al., Gene, 96:23 (1990)), were transferred into a 1.5 ml microcentrifuge tube, and mixed with 10μ1 of the supernatant recovered in EXAMPLE 2.2.C. This mixture was then stored for 30 minutes on ice. The mixture was subsequently incubated for 30 seconds at 42° C., and then chilled in ice again for 1–2 minutes. 0.5 ml of SOC medium (2% Bacto trypton, 0.5% Bacto yeast extract, 10 mM NaCl, 2.5 mM KCl, 10 mM MgCl$_2$, 10 mM MgSO$_4$, 20 mM glucose) was added to the tube and incubated at 37° C. for 1 hour with shaking. The cells were spread on LB Plate [containing 50–100 μg/ml ampicillin, 1 mg/plate X-gal (5-bromo-4-chloro-3-indolyl-β-D-galactoside), 0.5–1.0 mg/plate IPTG (isopropyl-β-D(−)-thiogalactopyranoside)] and incubated over night at 37° C. Under this condition, Escherichia coli cells transformed with php53B, the double-stranded target DNA, show white colonies, and Escherichia coli cells transformed with pUC18, heterologous DNA, show blue colonies.

The various conditions and the results of the transformation obtained under those conditions are shown in Table 3 and Table 4.

TABLE 3

| | Reaction Condition | | | | |
|---|---|---|---|---|---|
| No. | Homo.P. Type | Homo.P. Amount | Hetero.P. Type | Hetero.P. Amount | RecA Amount |
| 1 | 275 bases | 150 ng | — | — | 4.5 μg |
| 2 | 275 bases | 1 ng | lambda 500 bases | 150 ng | 4.5 μg |
| 3 | 275 bases | 1 ng | lambda 308 bases | 150 ng | 4.5 μg |
| 4 | 275 bases | 1 ng | salmon sperm DNA | 150 ng | 4.5 μg |
| 5 | 60 bases | 150 ng | — | — | 4.5 μg |
| 6 | 60 bases | 1 ng | lambda 500 bases | 150 ng | 4.5 μg |
| 7 | 60 bases | 1 ng | lambda 308 bases | 150 ng | 4.5 μg |
| 8 | 60 bases | 1 ng | salmon sperm DNA | 150 ng | 4.5 μg |

TABLE 4

The Result of Transformation[1]

| Reaction Condition No. | Number of white colonies | Number of blue colonies | Specificity (%)[2] |
|---|---|---|---|
| 1 | 838 | 44,672 | 1.8 |
| 2 | 762 | 263 | 74.3 |
| 3 | 813 | 230 | 77.9 |
| 4 | 844 | 237 | 78.1 |
| 5 | 13 | 6,558 | 0.2 |
| 6 | 644 | 211 | 75.3 |
| 7 | 676 | 202 | 77.0 |
| 8 | 688 | 181 | 79.2 |

[1] mean values obtained from the three repeated experiments are indicated.
[2] specificity (%) = number of white colonies ÷ (number of white colonies and number of blue colonies) × 100

The results summarized above show that, in a reaction containing the circular target DNA at the ratio of 1:100,000, although the reaction contained an extremely small amount of the homologous probe (1 ng) and 150 fold of the amount (150 ng) of the heterologous probe, the reduction in the reactivity was not observed. On the contrary, the results show that a remarkable enhancement of the specificity and the reactivity by adding the heterologous probe (especially when the 60 nucleotide probe was employed). The results achieved here are the same as the results achieved in Example 2.1 when the target DNA is present at a ratio of 1:10,000. The above results also show that the 308-nucleotide probe which has a partial sequence of lambda phage genome can be used as a heterologous probe.

3. Target DNA: heterologous DNA=1:10,000 (a probe of 30 nucleotides in length was used and GTPγS was used as a co-factor)

A. The Preparation of the Homologous Probe

The 30 nucleotide single-stranded probe (SEQ ID NO:6) containing the partial sequence of p53 cDNA was synthesized using a DNA synthesizer. The nucleotide probe was biotinylated at its 5'-end. The nucleotide sequence corresponding to this region of p53 cDNA is shown as SEQ ID NO:6.

B. The Preparation of the Heterologous Probe

In addition to the heterologous probe used in EXAMPLE 2.2, a single-stranded probe of 60 nucleotides in length (SEQ ID NO:7), which contained a partial sequence of lambda phage genome, synthesized according to conventional methods using DNA synthesizer (the nucleotide sequence of this region is indicated as SEQ ID NO: 7), and rRNA from E.coli (a mixture of 16S and 23S, manufactured by Boehringer-Mannheim GmbH) were also used as heterologous probes.

C. Homologous Pairing (Hybridization Reaction)

(a) The preparation of various probe/RecA protein complex

A single-stranded probe of 30 nucleotides in length containing a partial sequence of p53 cDNA and biotinylated at its 5'-end, which was prepared as in EXAMPLE 2.3.A, or a mixture of the said homologous probe and various heterologous probes described in EXAMPLE 2.3.B, was diluted in either distilled water or TE buffer (10 mM Tris-HCl, 1 mM EDTA, pH 7.5). The aliquot was transferred to a 0.6 ml microcentrifuge tube and was heated in the boiling water for 5 minutes to denature the double-stranded probe. The tube was rapidly chilled in ice water, then 0.9 μl of 10×reaction buffer [300 mM Tris-HCl (pH 7.5 at 37° C.), 20 mM MgCl$_2$, 4 mM DTT, 30% glycerol], 0.9 μl of 5 mM GTPγS solution, and RecA protein (manufactured by Boehringer-Mannheim GmbH) were added to the tube, and the mixture was allowed to react for 12 minutes at 37° C. after dilution with distilled water to the total volume of 9 μl.

(b) The preparation of probe/target, DNA complex 0.9 μl of 10×reaction buffer, 0.9 μl of 5 mM GTPγS solution, 0.9 μl of 0.2 M MgCl$_2$ solution, 245 pg. of php53B, which was double-stranded target DNA in circular form prepared in EXAMPLE 1 1, and 1 μg of pUC18, which was circular heterologous DNA (molar ratio of target DNA to heterologous DNA is 1:10,000) were mixed and diluted with distilled water to a total volume of 9 μl. This mixture was mixed with either the complex of homologous probe and RecA protein or the mixture of homologous probe/RecA protein complex and heterologous probe/RecA protein complex obtained from the reaction described above. The mixture thus obtained was subjected to the reaction for 60 minutes at 37° C. The amount of the homologous probe, the type and the amount of the heterologous probe, and the amount of RecA protein which were used in each reaction are shown in Table 5. In all the reactions, a final volume of the reactant was 18 μl.

D. Capturing/isolation by Magnetic Beads

20 μl of the magnetic beads coated with streptavidin, manufactured by DYNAL®, was transferred to a 0.6 ml microcentrifuge tube and was washed two times in 100 μl of 33 mM Tris-HCl and 50 mM NaCl (pH7.5) using Magnetic Beads Separation Rack (MAGNA-SEP™). After discarding the washing solution, whole volume of the hybridization-reaction solution was added to the microcentrifuge tube to be well mixed with the washed magnetic beads. The mixture was stored for 15 minutes at room temperature with stirring every 2–3 minutes. The magnetic beads were separated from the non-binding molecules using a Magnetic Beads Separation Rack. After discarding the supernatant, magnetic beads were washed twice in 100 μl of 33 mM Tris-HCl and 50 mM NaCl (pH7.5) solution for 5 minutes at 370C. After discarding the washing solution, the beads were suspended and mixed with 10 μl of 33 mM Tris-HCl and 200 mM NaCl (pH7.5), and then the mixture was heated to 85° C. for 8 minutes. The supernatant containing target DNA was recovered using the Magnetic Beads Separation Rack.

E. Transformation

100 μl of competent cells, which were prepared from Escherichia coli strain JM109 according to the method of Nojima et al. (Inoue H. et al., Gene, 96:23 (1990)), were transferred into a 1.5 ml microcentrifuge tube, and mixed with 2 μl of the supernatant recovered in D. This mixture was then stored for 30 minutes on ice. The mixture was subsequently incubated for 30 seconds at 42° C., and then chilled in the ice again for 1–2 minutes. 0.5 ml of SOC medium (2% Bacto trypton, 0.5% Bacto yeast extract, 10 mM NaCl, 2.5 mM KCl, 10 mM MgCl$_2$, 10 mM MGSO$_4$, 20 mM glucose) was added to the tube and incubated at 37° C. for 1 hour with shaking. The cells were spread on LB Plate [containing 50–100 μg/ml ampicillin, 1 mg/plate X-gal (5-bromo-4-chloro-3-indolyl-β-D galactoside), 0.5–1.0 mg/plate IPTG (isopropyl-β-D(−)-thiogalactopyranoside)], and incubated over night at 37° C. Under this condition, Escherichia coli transformed with php53B, the double-stranded target DNA, shows white colonies, and Escherichia coli transformed with pUC18, heterologous DNA, shows blue colonies. The various conditions and the results of the transformation obtained under those conditions are shown in Table 5 and Table 6.

TABLE 5

Reaction Condition

| No. | Homo.P. Amount | Hetero.P. Type | Hetero.P. Amount | RecA Amount |
|---|---|---|---|---|
| 1 | 150 ng | — | — | 4.5 μg |
| 2 | 25 ng | lambda 500 bases | 125 ng | 4.5 μg |
| 3 | 25 ng | lambda 308 bases | 125 ng | 4.5 μg |
| 4 | 25 ng | lambda 60 bases | 125 ng | 4.5 μg |
| 5 | 25 ng | salmon sperm DNA | 125 ng | 4.5 μg |
| 6 | 25 ng | E. coli rRNA | 125 ng | 4.5 μg |

TABLE 6

The Result of Transformation[1]

| Reaction Condition | Number of white colonies | Number of blue colonies | Specificity (%)[2] |
|---|---|---|---|
| 1 | 89 | 901 | 9.0 |
| 2 | 545 | 276 | 66.4 |
| 3 | 563 | 289 | 66.1 |
| 4 | 596 | 280 | 68.0 |
| 5 | 632 | 271 | 70.0 |
| 6 | 551 | 388 | 58.7 |

[1]mean values obtained from the three repeated experiments are indicated.
[2]specificity (%) = number of white colonies/(number of white colonies and number of blue colonies) × 100

The above results show that the specificity and the reactivity were remarkably enhanced by adding heterologous probe to the reaction when the 30 nucleotide homologous probe, as well as the 60-nucleotide and the 275-nucleotide homologous probe, were used. The results also show that the 60-nucleotide single-stranded DNA probe, containing the partial sequence of lambda phage genome, and rRNA derived from *Escherichia coli* (a mixture of 16S and 23 S) can be used as the heterologous probe.

EXAMPLE 3

Screening of Target cDNA from cDNA Library

Plasmids containing p53cDNA sequence were obtained from 5 μg of a cDNA library prepared from a commercially available human brain cDNA library (SUPER SCRIPT Human Brain cDNA Library manufactured by BRL). The ratio of p53 cDNA to the library DNA was determined by the colony hybridization reaction method and was about 1:100,000–1:200,000.

The double-stranded homologous probe of 275 bp and 60 bp sequence, and the single-stranded homologous probe of 30 bp, as prepared in EXAMPLE 1 and EXAMPLE 2, were used. The lambda DNA fragments, as prepared in EXAMPLE 1, were used as heterologous probe.

Homologous pairing, capturing/isolation by magnetic beads and transformation were performed in accordance with the methods described in EXAMPLE 2.2 and EXAMPLE 2.3. The obtained transformants were spread on LB Plate containing 50–100 μg/ml ampicillin, and incubated over night at 37°. 30 colonies were randomly selected from the ampicillin-resistant colonies obtained by each of the reactions, and plasmid DNA was extracted from each of the colonies by the Miniprep. method. (Quantum Prep® Plasmid Miniprep Kit manufactured by Bio Rad was used.)

After performing the PCR reaction using a primer that has the same sequence as the one used in the preparation of the 275 bp homologous probe and that is not biotinylated, agarose electrophoretic analysis was performed to determine, based on the presence of the 275 nucleotide fragments, whether or not the plasmid DNA extracted from each colony contained p53 cDNA. The specificity was calculated based on the following formula:

Specificity (%)=Number of PCR positive clones÷30×100

The various reaction conditions and the cDNA library screening results obtained under those reaction conditions are shown in Table 7 and 8.

TABLE 7

| No. | Homo.P. Type | Homo.P. Amount | Hetero.P. Type | Hetero.P. Amount | RecA Amount |
|---|---|---|---|---|---|
| 1 | 30 bases | 150 ng | — | — | 4.5 μg |
| 2 | 30 bases | 5 ng | lambda DNA fragment | 145 ng | 4.5 μg |
| 3 | 60 bases | 150 ng | — | — | 4.5 μg |
| 4 | 60 bases | 5 ng | lambda DNA fragment | 145 ng | 4.5 μg |
| 5 | 275 bases | 150 ng | — | — | 4.5 μg |
| 6 | 275 bases | 5 ng | lambda DNA fragment | 145 ng | 4.5 μg |

TABLE 8

| No. | Number of Amp[r] Colonies | Specificity (%) |
|---|---|---|
| 1 | 1,778 | 6.6 |
| 2 | 248 | 50.0 |
| 3 | 1,119 | 3.3 |
| 4 | 115 | 60.0 |
| 5 | 7,871 | 0.0 |
| 6 | 130 | 66.7 |

From the above results, in the screening of target cDNA from an actual cDNA library, it is confirmed that the specificity is greatly improved by the addition of heterologous probe.

The present invention has made it possible to target, enrich, detect and/or isolate the double-stranded target DNA molecule existing in the DNA sample in extremely small amount with high efficiency and specificity by using the short-strand homologous probe and heterologous probe. The present invention is expected to be applied to isolating or cloning a target gene from a cDNA or a genomic DNA mixture; screening for a target gene in various gene libraries, amplifying a target DNA sequence or mapping genes using RecA like recombinases; performing sequence-specific modification of or cleaving a target DNA using oligonucleotides; and in-situ hybridizing and in vivo gene targeting performed in living cells using RecA-like recombinase.

SUMMARY OF SEQUENCES

SEQ ID NO:1 is a double-stranded DNA fragment of p53 cDNA.

SEQ ID NO:2 is a double-stranded DNA fragment of p53 cDNA.

SEQ ID NO:3 is a double-stranded DNA fragment of lambda phage genomic DNA sequence.

SEQ ID NO:4 is a double-stranded DNA fragment of lambda phage genomic DNA sequence.

SEQ ID NO:5 is a double-stranded DNA fragment of lambda phage genomic DNA sequence.

SEQ ID NO:6 is a single-stranded DNA probe corresponding to a region of p53 cDNA.

SEQ ID NO:7 is a single-stranded DNA probe corresponding to a region of lambda phage genomic DNA.

SEQ ID NO:8 is a double-stranded DNA fragment of p53 cDNA.

SEQ ID NO:9 is a double-stranded DNA fragment of p53 cDNA.

SEQ ID NO:10 is a double-stranded DNA fragment of p53 cDNA.

SEQ ID NO:11 is an oligonucleotide primer for p53 cDNA.

SEQ ID NO:12 is an oligonucleotide primer for p53 cDNA.

SEQ ID NO:13 is an oligonucleotide primer for p53 cDNA.

SEQ ID NO:14 is an oligonucleotide primer for p53 cDNA.

SEQ ID NO:15 is an oligonucleotide primer for p53 cDNA.

SEQ ID NO:16 is an oligonucleotide primer for p53 cDNA.

SEQ ID NO:17 is an oligonucleotide primer for p53 cDNA.

SEQ ID NO:18 is an oligonucleotide primer for lambda phage genomic DNA.

SEQ ID NO:19 is an oligonucleotide primer for lambda phage genomic DNA.

SEQ ID NO:20 is an oligonucleotide primer for lambda phage genomic DNA.

SEQ ID NO:21 is an oligonucleotide primer for lambda phage genomic DNA.

SEQ ID NO:22 is an oligonucleotide primer for lambda phage genomic DNA.

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects as illustrative only and not as restrictive. The scope of the invention is, therefore, indicated by the appended claims rather than by the foregoing description. All changes which come within the meaning and range of the equivalence of the claims are to be embraced within the scope of the claims.

What is claimed is:

1. A method for improving specificity of homologous pairing or strand exchange or a combination of homologous pairing and strand exchange between a double-stranded target nucleic acid sequence and a homologous nucleic acid probe by using a RecA-like recombinase, comprising the steps of:
   (a) providing at least one recombinase, at least one homologous probe, and at least one heterologous probe, wherein the probes are bound to the recombinase, and
   (b) mixing the recombinase-bound homologous probe and the recombinase-bound heterologous probe with the double-stranded nucleic acid target sequence in a sample,
   wherein the weight ratio of the homologous probe to the heterologous probe is about 1:5 to about 1:500, wherein the combination of recombinase-bound heterologous probe and recombinase-bound homologous probe improves the specificity of the homologous pairing or strand exchange or combination of homologous pairing and strand exchange relative to a method wherein recombinase-bound homologous probe is used alone.

2. The method of claim 1, wherein the double-stranded nucleic acid target sequence is double-stranded target DNA.

3. The method of claim 1, wherein the step (a) provides at least two types of homologous probes.

4. The method of claim 3, wherein the homologous probes are two types of homologous probes which are sufficiently complementary to each other.

5. The method of claim 1, wherein the homologous probe is at least 15 nucleic acid residues in length.

6. The method of claim 5, wherein the homologous probe is about 15 to 2000 nucleic acid residues in length.

7. The method of claim 1, wherein the homologous probe comprises a label or a ligand.

8. The method of claim 1, wherein the homologous probe is a double-stranded DNA probe.

9. The method of claim 1, wherein the homologous probe is a single-stranded DNA probe.

10. The method of claim 1, wherein the heterologous probe is about 15 bases or longer.

11. The method of claim 1, wherein the heterologous probe is a single-stranded DNA probe.

12. The method of claim 1, wherein the heterologous probe is a RNA probe.

13. The method of claim 1, wherein the weight ratio of the homologous probe to the heterologous probe is about 1:5 to about 1:250.

14. The method of claim 1, wherein the RecA-like recombinase is derived from a prokaryote.

15. The method of claim 13, wherein the RecA-like recombinase is derived from *Escherichia coli*.

16. The method of claim 14, wherein the RecA-like recombinase is RecA.

17. A method for enriching or isolating or a combination of enriching and isolating a double-stranded nucleic acid target sequence in a sample by using a RecA-like recombinase, comprising the steps of:
   (a) providing a homologous probe which has a label or a ligand and which is bound to at least one recombinase, and a heterologous probe bound to said at least one recombinase;
   (b) reacting the recombinase-bound homologous probe and the recombinase-bound heterologous probe with the double-stranded nucleic acid target sequence under conditions which promote the formation of a complex of the double stranded nucleic acid target sequence and the homologous probe in the reaction mixture, wherein the weight ratio of the homologous probe to the heterologous probe is about 1:5 to about 1:500;
   (c) contacting the reaction mixture with a solid support designed to selectively bind the complex of the double-stranded nucleic acid target sequence and the homologous probe;
   (d) removing non-bound molecules from the solid support; and
   (e) treating the solid support to release the double-stranded nucleic acid target sequence which is selectively bound to the solid support through the complex.

18. The method of claim 17, wherein the double-stranded nucleic acid target sequence is double-stranded target DNA.

19. The method of claim 18, wherein the sample is a cDNA or a genomic DNA library, and the double-stranded target DNA is inserted to a vector capable of transforming or transfecting a suitable bacterial host.

20. The method of claim 19 further comprising the steps of:
   (a) providing suitable host cells which are capable of being transformed or transfected by the double-stranded target DNA inserted into a vector;
   (b) transforming or transfecting the host cells with the target DNA fraction released from the solid phase; and
   (c) selecting transformed or transfected cells containing said target DNA.

21. The method of claim 18, wherein the sample is a clinical specimen containing a mixture of cDNA or genomic DNA.

22. The method of claim 17, wherein the label or ligand is biotin or digoxigenin.

23. The method of claim 17, wherein the solid phase comprises magnetic or paramagnetic beads surfacely bound to avidin, streptavidin, or anti-digoxigenin antibody.

24. The method of claim 17, wherein at least two types of homologous probes are provided.

25. The method of claim 24, wherein two types of homologous probes which are sufficiently complementary to each other are provided.

26. The method of claim 17, wherein the RecA-like recombinase is derived from prokaryote.

27. The method of claim 26, wherein the RecA-like recombinase is derived from *Escherichia coli*.

28. The method of claim 17, wherein the heterologous probe is at least 15 nucleic acid residues in length.

29. The method of claim 17, wherein the homologous probe is at least 15 nucleic acid residues in length.

30. The method of claim 17, wherein the weight ratio of the homologous probe to the heterologous probe is about 1:1 to about 1:500.

31. A method for detecting a double-stranded nucleic acid target sequence in a sample of cells by in situ hybridization using a RecA-like recombinase, comprising the steps of:

(a) providing a homologous probe and a heterologous probe, wherein the probes are bound to the recombinase;

(b) adding the recombinase-bound homologous probe and the recombinase-bound heterologous probe to the sample of cells under a condition to promote the reaction of the homologous probe with the double-stranded nucleic acid target sequence; and (c) removing the recombinase-bound homologous probes which have not reacted with the double-stranded nucleic acid target sequence;

wherein said double-stranded nucleic acid target sequence is detected in a sample of cells by in situ hybridization using a RecA-like recombinase.

32. The method of claim 31, wherein the weight ratio of the homologous probe to the heterologous probe is about 1:5 to about 1:250.

33. The method of claim 31, wherein at least two types of homologous probes are provided.

34. The method of claim 33, wherein two types of homologous probes which are sufficiency complementary to each other are employed.

35. The method of claim 31, wherein the heterologous probe is of 15 bases or longer.

36. The methods of claims 1, 17 or 31, wherein the homologous and heterologous probes are bound to recombinase in the presence of a co-factor.

37. The method of claim 36, wherein the RecA-like recombinase is derived from *Escherichia coli*.

38. The method of claim 36, wherein the cofactor is selected from a group consisting of GTP S, a mixture of ATP S and ADP, a mixture of ADP and $AlF_4^-$ (aluminum nitrate and sodium fluoride), a mixture of ATP and $AlF_4^-$ (aluminum nitrate and sodium fluoride), a mixture of dADP and $AlF_4^-$ (aluminum nitrate and sodium fluoride), or a mixture of dATP and $AlF_4^-$ (aluminum nitrate and sodium fluoride).

39. The method of claim 38, wherein the cofactor is GTP S.

40. A method for targeting a double-stranded nucleic acid target sequence in a sample of living cells by an in vivo gene targeting method using a RecA-like recombinase, comprising the steps of:

(a) providing a recombinase-bound homologous probe and a recombinase-bound heterologous probe;

(b) introducing the recombinase-bound homologous probe and the recombinase-bound heterologous probe into the living cells;

(c) incubating the living cells containing the recombinase-bound homologous probe and the recombinase-bound heterologous probe for a sufficient period of time to allow the recombinase-bound homologous probe to be transformed into the genome of the cells;

wherein said double-stranded nucleic acid target sequence is targeted in a sample of living cells by an in vivo gene targeting method using a RecA-like recombinase.

41. The method of claim 40, wherein the weight ratio of the homologous probe to the heterologous probe is about 1:5 to about 1:250.

42. A kit for improving specificity of homologous pairing or strand exchange or a combination of homologous pairing and strand exchange between a double-stranded target nucleic acid sequence and a homologous nucleic acid probe according to the method of claim 1, comprising a RecA-like recombinase, a cofactor, at least one heterologous probe, a solid phase designed to trap a complex of a double-stranded nucleic acid target sequence and at least one homologous probe having a label or ligand, and washing buffer, wherein the combination of recombinase-bound heterologous probe and recombinase-bound homologous probe improves the specificity of the homologous pairing or strand exchange or combination of homologous pairing and strand exchange relative to a method wherein recombinase-bound homologous probe is used alone.

43. The kit of claim 42, wherein the weight ratio of the homologous probe to the heterologous probe is about 1:1 to about 1:500.

44. The method of claim 1 further comprising the step of enriching or isolating the target sequence.

45. The method of claim 1 further comprising the step of detecting the target sequence.

46. The kit of claim 42, wherein the double-stranded nucleic acid target sequence is double-stranded target DNA.

47. The kit of claim 42, wherein the homologous probes are at least two homologous probes.

48. The kit of claim 47, wherein the homologous probes are two homologous probes which are sufficiently complementary to each other.

49. The kit of claim 42, wherein the homologous probe is at least 15 nucleic acid residues in length.

50. The kit of claim 49, wherein the homologous probe is 15 to 2000 nucleic acid residues in length.

51. The kit of claim 42, wherein the homologous probe is a double-stranded DNA probe.

52. The kit of claim 42, wherein the homologous probe is a single-stranded DNA probe.

53. The kit of claim 42, wherein the heterologous probe is at least 15 bases.

54. The kit of claim 42, wherein the heterologous probe is a single-stranded DNA probe.

55. The kit of claim 42, wherein the heterologous probe is a RNA probe.

56. The kit of claim 42, wherein the RecA-like recombinase is derived from a prokaryote.

57. The kit of claim 56, wherein the RecA-like recombinase is derived from *Escherichia coli*.

58. The kit of claim 56, wherein the RecA-like recombinase is RecA.

* * * * *

UNITED STATES PATENT AND TRADEMARK OFFICE
CERTIFICATE OF CORRECTION

PATENT NO.    : 6,335,164 B1
DATED         : January 1, 2002
INVENTOR(S)   : Koji Kigawa et al.

It is certified that error appears in the above-identified patent and that said Letters Patent is hereby corrected as shown below:

Column 10,
Line 14, change "1 [g" to -- 1$\mu$ g --.
Line 60, change "1 lg" to -- 1$\mu$ g --.

Column 22,
Line 38, change "370C" to -- 37°C --.

Column 39,
Line 62, change "The method of claim 13" to -- The method of claim 14 --.

Column 41,
Line 35, change "The methods of claims 1, 17, or 31, wherein" to -- The method of claim 1, wherein --.
Lines 41-42, change "consisting of GTP S, a mixture of ATP S and ADP," to -- consisting of GTP ϒ S, a mixture of ATP ϒ S and ADP, --.
Line 48, change "wherein the cofactor is GTP S" to -- wherein the cofactor is GTP ϒ S --.

Signed and Sealed this

Twenty-third Day of July, 2002

Attest:

Attesting Officer

JAMES E. ROGAN
*Director of the United States Patent and Trademark Office*